(12) United States Patent
Lynn et al.

(10) Patent No.: US 11,728,041 B2
(45) Date of Patent: Aug. 15, 2023

(54) REAL-TIME TIME SERIES MATRIX PATHOPHYSIOLOGIC PATTERN PROCESSOR AND QUALITY ASSESSMENT METHOD

(71) Applicant: Lawrence A. Lynn, Columbus, OH (US)

(72) Inventors: Eric N. Lynn, Villa Ridge, MO (US); Lawrence A. Lynn, Columbus, OH (US)

(*) Notice: Subject to any disclaimer, the term of this patent is extended or adjusted under 35 U.S.C. 154(b) by 667 days.

(21) Appl. No.: 14/626,790

(22) Filed: Feb. 19, 2015

(65) Prior Publication Data
US 2015/0227713 A1 Aug. 13, 2015

Related U.S. Application Data

(63) Continuation-in-part of application No. 13/677,291, filed on Nov. 14, 2012, now abandoned, and a
(Continued)

(51) Int. Cl.
*G16H 50/70* (2018.01)
*G06F 16/9535* (2019.01)
(Continued)

(52) U.S. Cl.
CPC ......... *G16H 50/70* (2018.01); *G06F 16/9535* (2019.01); *G06Q 10/063* (2013.01);
(Continued)

(58) Field of Classification Search
None
See application file for complete search history.

(56) References Cited

U.S. PATENT DOCUMENTS 5,398,682 A 3/1995 Lynn
5,804,370 A 9/1998 Romaschin et al.
(Continued)

FOREIGN PATENT DOCUMENTS

JP 4435681 B2 3/2010
WO WO-2006061644 A1 * 6/2006 ........... C12Q 1/6883
(Continued)

OTHER PUBLICATIONS

Norris, Patrick Roger. "Toward New Vital Signs: Tools and Methods for Physiologic Data Capture, Analysis, and Decision Support in Critical Care." Order No. 3230579 Vanderbilt University, 2006. Ann Arbor: ProQuest. Web. Mar. 21, 2023. (Year: 2006).*
(Continued)

*Primary Examiner* — Lena Najarian
(74) *Attorney, Agent, or Firm* — Vorys, Sater, Seymour and Pease LLP; Rex W. Miller, II

(57) ABSTRACT

A medical monitoring device for analysis of a set of physiologic and laboratory data and for providing a real time or near real time correlation metric for a distress condition is described herein. The medical monitoring device can include a memory storage that comprises a first set of definitions of rise and fall patterns of said physiologic and laboratory data, each of the rise and fall patterns being indicative of a physiological occurrence, a second set of definitions of time series matrix patterns of said rise and fall patterns, the time series matrix patterns being indicative of a distress condition, and a pre-determined correlation metric for each of at least a portion of the time series matrix patterns with reference to the distress condition. The medical monitoring device can also include a monitor to identify the time series matrix patterns in data in memory storage.

7 Claims, 36 Drawing Sheets

Related U.S. Application Data continuation-in-part of application No. 12/437,385, filed on May 7, 2009, now abandoned, and a continuation-in-part of application No. 12/437,417, filed on May 7, 2009, now Pat. No. 9,053,222.

(60) Provisional application No. 61/629,147, filed on Nov. 14, 2011, provisional application No. 61/629,164, filed on Nov. 14, 2011, provisional application No. 61/200,162, filed on Nov. 25, 2008, provisional application No. 61/200,162, filed on Nov. 25, 2008, provisional application No. 61/126,906, filed on May 7, 2008, provisional application No. 61/126,906, filed on May 7, 2008.

(51) Int. Cl.
  G16H 10/60 (2018.01)
  G16H 50/20 (2018.01)
  G16H 15/00 (2018.01)
  G06Q 10/063 (2023.01)

(52) U.S. Cl.
  CPC .............. G16H 10/60 (2018.01); G16H 15/00 (2018.01); G16H 50/20 (2018.01)

(56) References Cited

U.S. PATENT DOCUMENTS

| | | | |
|---|---|---|---|
| 5,865,174 | A | 2/1999 | Kloeppel |
| 6,159,683 | A | 12/2000 | Romaschin et al. |
| 6,683,609 | B1 | 1/2004 | Baron, Sr. et al. |
| 7,252,637 | B2 | 8/2007 | Ebner et al. |
| 7,664,601 | B2 | 2/2010 | Daly, Jr. |
| 7,792,642 | B1 | 9/2010 | Neilley et al. |
| 8,663,107 | B2 | 3/2014 | Kiani |
| 9,042,952 | B2 | 5/2015 | Lynn et al. |
| 2002/0002327 | A1 | 1/2002 | Grant et al. |
| 2002/0030682 | A1 | 3/2002 | Eberlein |
| 2002/0099273 | A1 | 7/2002 | Bocionek et al. |
| 2003/0158466 | A1 | 8/2003 | Lynn et al. |
| 2003/0194752 | A1 | 10/2003 | Anderson et al. |
| 2004/0048264 | A1 | 3/2004 | Stoughton et al. |
| 2004/0128163 | A1 | 7/2004 | Goodman et al. |
| 2005/0182333 | A1 | 8/2005 | Nagata et al. |
| 2006/0149144 | A1* | 7/2006 | Lynn ................. A61B 5/00 600/323 |
| 2006/0235324 | A1 | 10/2006 | Lynn |
| 2006/0253300 | A1 | 11/2006 | Somberg et al. |
| 2008/0091088 | A1 | 4/2008 | Kiani |
| 2008/0235049 | A1 | 9/2008 | Morita et al. |
| 2008/0275349 | A1 | 11/2008 | Halperin et al. |
| 2009/0171169 | A1 | 7/2009 | Nagata |
| 2011/0046498 | A1 | 2/2011 | Klap et al. |

FOREIGN PATENT DOCUMENTS

| | | | |
|---|---|---|---|
| WO | 2009137682 | A1 | 11/2009 |
| WO | 2010065262 | A1 | 6/2010 |
| WO | 2013/074708 | A1 | 5/2013 |

OTHER PUBLICATIONS

Richard J. Allen and Timothy C. Elston; "From Physics to Pharmacology?"; Department of Pharmocology, University of North Carolina at Chapel Hill, Chapel Hill, NC, US; Reports on Progress on Physics; Institute of Physics Publishing; vol. 74, No. 1; Dec. 3, 2010; pp. 1-19; stacks.iop.org/RoPP/74/016601.

Sergey M. Zuev, et al.; "Sepsis Progression and Outcome: A Dynamical Model"; Theoretical Biology and Medical Modelling, Biomed Central, Ltd.; London, GB; vol. 3, No. 1; Feb. 15, 2006; pp. 1-15; http://tbiomed.com/content/3/1/8.

Fawcett, Tom, ROC Graphs: Notes and Practical Considerations for Data Mining Researchers, Hewlett-Packard Company, 2003, 28 pages.

Guven et al., Diagnostic Value of Procalcitonin Levels as an Early Indicator of Sepsis, Am JEmerg Med, 2002m pp. 202-206, vol. 20.

Haumptman et al., Evaluation of the Sensitivity and Specificity of Diagnostic Criteria for Sepsis in Dogs, Veterinary Surgery, 1997, pp. 393-379, vol. 26.

International Search Report for International (PCT) Patent Application No. PCT/US2012/065124, dated Jul. 23, 2015, 6 pages.

Rao, Singiresu, Engineering Optimization Theory: Advantages of Random Search Methods, 2009, pp. 314-317.

Mar. 11, 2016—U.S. Non-Final Office Action—U.S. Appl. No. 12/437,385.

PCT—International Preliminary Report on Patentability, for PCT application No. PCT/US2014/019530; dated Sep. 1, 2015; 8 Pages.

PCT—International Preliminary Report on Patentability, for PCT application No. PCT/US2014/019556; dated Sep. 1, 2015; 9 Pages.

PCT—International Preliminary Report on Patentability, for PCT application No. PCT/US2014/019572; dated Sep. 1, 2015; 6 Pages.

PCT—International Preliminary Report on Patentability, for PCT application No. PCT/US2014/019577; dated Sep. 1, 2015; 8 Pages.

PCT—International Preliminary Report on Patentability, for PCT application No. PCT/US2014/019637; dated Sep. 1, 2015; 8 Pages.

PCT—International Preliminary Report on Patentability, for PCT application No. PCT/US2014/019442; dated Sep. 1, 2015; 6 Pages.

PCT—International Preliminary Report on Patentability, for PCT application No. PCT/US2014/019582; dated Sep. 1, 2015; 7 Pages.

PCT—International Preliminary Report on Patentability, for PCT application No. PCT/US2014/019587; dated Sep. 1, 2015; 6 Pages.

PCT—International Preliminary Report on Patentability, for PCT application No. PCT/US2014/019625; dated Sep. 1, 2015; 15 Pages.

Non-Final Office Action issued in U.S. Appl. No. 12/629,407, dated Oct. 2, 2015, 19 Pages.

Non-Final Office Action for U.S. Appl. No. 12/777,171, dated Mar. 5, 2015, 12 pages.

Non-Final Office Action for U.S. Appl. No. 13/392,827, dated Mar. 27, 2015, 18 pages.

Non-Final Office Action for U.S. Appl. No. 13/677,295, dated Apr. 8, 2015, 15 pages.

Non-Final Office Action for U.S. Appl. No. 13/844,381, dated Apr. 9, 2015, 21 pages.

Non-Final Office Action for U.S. Appl. No. 13/844,212, dated Apr. 9, 2015, 21 pages.

Non-Final Office Action for U.S. Appl. No. 13/844,404, dated Apr. 9, 2015, 18 pages.

Non-Final Office Action for U.S. Appl. No. 13/843,481, dated Apr. 9, 2015, 19 pages.

Non-Final Office Action for U.S. Appl. No. 14/193,757, dated May 8, 2015, 15 pages.

Final Office Action for U.S. Appl. No. 12/437,385, dated May 14, 2015, 31 pages.

Non-Final Office Action for U.S. Appl. No. 14/193,829, dated May 22, 2015, 17 pages.

Final Office Action issued in U.S. Appl. No. 13/843,481, dated Dec. 21, 2015, 26 pages.

Final Office Action issued in U.S. Appl. No. 13/844,381, dated Dec. 17, 2015, 25 pages.

Final Office Action issued in U.S. Appl. No. 13/844,212, dated Dec. 17, 2015, 24 pages.

Final Office Action issued in U.S. Appl. No. 13/844,404, dated Dec. 17, 2015, 27 pages.

Final Office Action issued in U.S. Appl. No. 13/677,295, dated Dec. 11, 2015, 20 pages.

Final Office Action issued in U.S. Appl. No. 14/193,376, dated Jan. 15, 2016, 26 pages.

Final Office Action issued in U.S. Appl. No. 14/193,829, dated Dec. 23, 2015, 22 pages.

Final Office Action issued in U.S. Appl. No. 14/193,757, dated Jan. 22, 2016, 30 pages.

(56) References Cited

OTHER PUBLICATIONS

European Search Report, for 12850333.1-1901/2780884 PCT/US2012065129, dated Jan. 14, 2016, 6 pages.

* cited by examiner

200

Scenarios

| Scenario | FallInPlatelets | Platelets | Result | Explanation |
|---|---|---|---|---|
| #1 | 1 | A | Specificity 70.59% | Anchor Found |
| #2 | 0 | A | No Effect | All Dependencies Met but Anchor Not Found |
| #3 | 0 | U | Potential 70.59% (Platelets) | Dependencies Not Available |

1602 points to the header row; 1606 points to "Result"; 1604 points near the header.

| Scenarios | | | | | | Result | Explanation |
|---|---|---|---|---|---|---|---|
| Scenario | Inflammatory/Injury | RiseInNeutrophils | FallinPlatelets | Neutrophil Abs | Platelets | | |
| #1 | 1 | 1 | 1 | A | A | Specificity 100.00% | Anchor Found |
| #2 | 0 | 0 | 1 | A | A | No Effect | All Dependencies Met but Anchor Not Found |
| #3 | 0 | 0 | 0 | U | A | No Effect | Though Neutrophil Abs is Unavailable the Fact that No FallinPlatelets Occurrences was Found Meant that this Stream Could Not Alter the Result |
| #4 | 0 | 0 | 1 | U | A | Potential 100.00% (Neutrophil Abs) | Neutrophil Abs is Unavailable and Since FallinPlatelets did Identify Occurrences there is a Potential that the Missing Stream could Cause an Identification of the Anchor Occurrence |
| #5 | 0 | 1 | 1 | A | A | No Effect | Anchor Not Found (Because RiseInNeutrophils is Too Far Away from FallinPlatelets) and All Dependencies are Available |
| #6 | 0 | 0 | 0 | U | U | Potential 100.00% (Neutrophil Abs, Platelets) | Since All Dependencies Are Unavailable We have Potential |

FIG. 18

| Scenarios | Inflammatory/InjuryIndicator | RiseInNeutrophils | RiseInWBC | HighWBC | Neutrophil Abs | WBC | Result | Explanation |
|---|---|---|---|---|---|---|---|---|
| #1 | 1 | 1 | 0 | 1 | A | A | Specificity 58.82% | Anchor Found |
| #2 | 0 | 0 | 0 | 0 | A | A | No Effect | All Dependencies Met but Anchor Not Found |
| #3 | 0 | 0 | 0 | 0 | A | U | Potential 58.82% (WBC) | WBC is Unavailable and its Availability Could Change the Identification of the Anchor |
| #4 | 0 | 0 | 0 | 0 | U | U | Potential 58.82% (Neutrophil Abs, WBC) | Unavailable Dependencies Could Change the Identification of the Anchor. Since there are More than One, We Indicate Bothe as Part of the Potential |
| #5 | 1 | 0 | 1 | 0 | U | A | Specificity 58.82% | Anchor Found |

| Scenarios | Sepsis | Inflammatory/Injury | FallinBicarb | RiseInNeutrophils | FallinPlatelets | Neutrophil Abs | Platelets | Bicarbonate | HCO3 Arterial | TCO2 Arterial | Result | Explanation |
|---|---|---|---|---|---|---|---|---|---|---|---|---|
| Scenario #1 | 1 | 1 | 1 | 1 | 1 | A | A | A | A | A | Specificity 82.35% | Anchor Found |
| #2 | 0 | 0 | 0 | 0 | 1 | A | A | A | A | A | No Effect | All Dependencies Met but Anchor Not Found |
| #3 | 1 | 0 | 1 | 0 | 1 | U | A | U | U | A | Specificity 82.35% | Anchor Found |
| #4 | 0 | 0 | 0 | 1 | 1 | A | A | U | U | U | Potential 82.35% (Bicarbonate, HCO3, Arterial, TCO2, Arterial) | Anchor Not Found (Because RiseInNeutrophils is Too Far Away from FallinPlatelets) and Unavailable Streams could have Supplied an Occurrence that would have Caused Identification |
| #5 | 0 | 0 | 0 | 0 | 0 | A | A | A | U | A | Potential 82.35% (HCO3, Arterial) | Anchor Not Found and HCO3, Arterial was Unavailable and if Available could have Supplied an Occurrence that would have Caused Identification |
| #6 | 0 | 0 | 0 | 0 | 0 | A | U | A | A | A | No Effect | Though Platelets was Unavailable, Since RiseInNeutrophils Produced No Occurrences the Availability of Platelets Could Not Affect the Outcome and Therefore We Cannnot Identify Potential |
| #7 | 0 | 0 | 0 | 1 | 0 | A | U | A | A | A | Potential 82.35% (Platelets) | Platelets are Unavailable and Since the RiseInNeutrophils Produced Occurrences the Availability of Platelets could Trigger Identification and Therefore we Identify Potential |

Smith, Jane
Summary
Trending Sepsis (0.7%/Hour)
Sepsis Specification (> 60%)
Top Specified Conditions
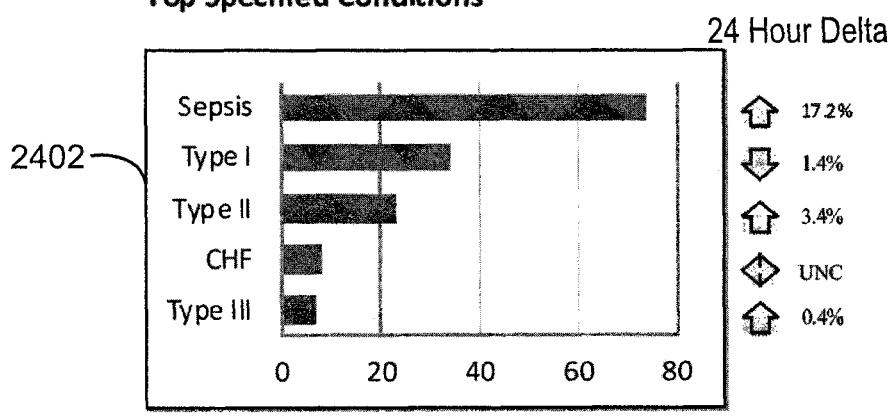
Top 28 Hour Deltas
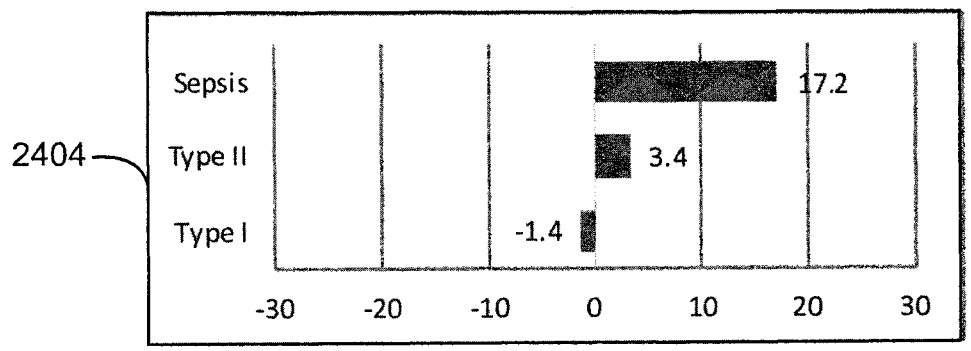
2400
FIG. 24

2500

2600

> Specificity: 74% <

2900

RSM Search: Sepsis

| Patient # | Name | Physician | Dept. | Specificity | Specificity 28 Hour Δ | Potential | Potential 28 Hour Δ |
|---|---|---|---|---|---|---|---|
| 3901587258 | Hardgrove, Sheila | Jones, Phil | CCU | 87% | +12 | 91% | +17 |
| 4278564286 | Jeffries, Frank | Wilberforce, Anne | Floor 3 | 87% | +9 | 91% | +7 |
| 3901587258 | Hardgrove, Sheila | Jones, Phil | CCU | 87% | +12 | 91% | +17 |
| 4278564286 | Jeffries, Frank | Wilberforce, Anne | Floor 3 | 87% | +9 | 91% | +7 |
| 1223435786 | Perez, Ben | Hernandez, Joseph | Floor 3 | 64% | +4 | 72% | -1 |
| 8741843765 | Tiponi, Flo | Wilberforce, Anne | CCU | 53% | +2 | 58% | +4 |
| 9428756941 | Castle, Brenda | Wilberforce, Anne | CCU | 45% | +3 | 45% | -3 |
| 8786878790 | Moore, Esther | Lee, Bill | CCU | 43% | -12 | 53% | -23 |
| 8952750987 | Jarkowski, Quintin | Hernandez, Joseph | CCU | 34% | +2 | 56% | +4 |
| 3452324215 | Smith, Jim | Jones, Phil | ICU | 34% | -3 | 42% | -2 |
| 6758674933 | Walker, Jennifer | Hernandez, Joseph | Floor 3 | 23% | 0 | 23% | 0 |
| 4956345234 | White, Jasper | Lee, Bill | CCU | 8% | -12 | 12% | -23 |

FIG. 30

Physician: Hernandez, Joseph

Rank By: Specificity

3106

3102

| Patient # | Name | Dept. | Condition | Specificity | Specificity 28 Hour Δ | Potential | Potential 28 Hour Δ |
|---|---|---|---|---|---|---|---|
| 1223435786 | Perez, Ben | Floor 3 | Sepsis | 64% | +4 | 72% | -1 |
| 1223435786 | Perez, Ben | Floor 3 | Condition 8 | 61% | 0 | 61% | -8 |
| 8952750987 | Jarkowski, Quintin | CCU | Condition 8 | 58% | -12 | 59% | -15 |
| 1223435786 | Perez, Ben | Floor 3 | Condition 6 | 58% | 0 | 41% | 0 |
| 1223435786 | Perez, Ben | Floor 3 | Condition 7 | 57% | 0 | 59% | -1 |
| 8952750987 | Jarkowski, Quintin | CCU | Condition 6 | 53% | -4 | 56% | -12 |
| 1223435786 | Perez, Ben | Floor 3 | Condition 5 | 45% | -1 | 48% | +1 |
| 8952750987 | Jarkowski, Quintin | CCU | Condition 4 | 43% | -8 | 47% | -12 |
| 8952750987 | Jarkowski, Quintin | CCU | Condition 2 | 42% | -5 | 43% | -10 |
| 8952750987 | Jarkowski, Quintin | CCU | Condition 5 | 41% | -13 | 48% | -14 |
| 1223435786 | Perez, Ben | Floor 3 | Condition 3 | 39% | -1 | 41% | -5 |
| 8952750987 | Jarkowski, Quintin | CCU | Condition 3 | 36% | -3 | 39% | -2 |

Physician: Wilberforce, Anne ▽ — 3206

Rank By: Potential ▽
3202

| Patient # | Name | Dept. | Condition | Specificity | Specificity 28 Hour Δ | Potential | Potential 28 Hour Δ |
|---|---|---|---|---|---|---|---|
| 8741843765 | Tiponi, Flo | CCU | Condition 3 | 89% | +8 | 95% | +7 |
| 9428756941 | Castle, Brenda | CCU | Condition 4 | 92% | +12 | 94% | -4 |
| 4278564286 | Jeffries, Frank | Floor 3 | Sepsis | 87% | +9 | 91% | +7 |
| 4278564286 | Jeffries, Frank | Floor 3 | Condition 10 | 36% | -23 | 84% | +18 |
| 9428756941 | Castle, Brenda | CCU | Condition 8 | 72% | -18 | 74% | -17 |
| 4278564286 | Jeffries, Frank | Floor 3 | Condition 6 | 58% | -4 | 72% | +8 |
| 4278564286 | Jeffries, Frank | Floor 3 | Condition 8 | 52% | +8 | 67% | +20 |
| 4278564286 | Jeffries, Frank | Floor 3 | Condition 7 | 58% | +4 | 64% | +6 |
| 8741843765 | Tiponi, Flo | CCU | Condition 6 | 61% | 0 | 61% | 0 |
| 4278564286 | Jeffries, Frank | Floor 3 | Condition 5 | 55% | +2 | 58% | -6 |
| 8741843765 | Tiponi, Flo | CCU | Sepsis | 53% | +2 | 58% | +4 |
| 4278564286 | Jeffries, Frank | Floor 3 | Condition 4 | 34% | -5 | 54% | +10 |

Department: CCU

Rank By: Potential 28 Hour Change — 3306

3304

| Potential 28 Hour Δ | Potential | Patient # | Name | Dept. | Condition | Specificity | Specificity 28 Hour Δ |
|---|---|---|---|---|---|---|---|
| -23 | 64% | 8786878790 | Moore, Esther | Lee, Bill | Condition 7 | 62% | -18 |
| -23 | 53% | 8786878790 | Moore, Esther | Lee, Bill | Sepsis | 43% | -1 |
| -23 | 12% | 4956345234 | White, Jasper | Lee, Bill | Sepsis | 8% | -12 |
| +23 | 43% | 4956345234 | White, Jasper | Lee, Bill | Condition 4 | 23% | -4 |
| -19 | 28% | 8741843765 | Tiponi, Flo | Wilberforce, Anne | Condition 10 | 24% | -4 |
| +18 | 54% | 8786878790 | Moore, Esther | Lee, Bill | Condition 4 | 23% | -4 |
| -17 | 74% | 9428756941 | Castle, Brenda | Wilberforce, Anne | Condition 8 | 72% | -18 |
| +17 | 91% | 3901587258 | Hardgrove, Sheila | Jones, Phil | Sepsis | 87% | +12 |
| +17 | 91% | 3901587258 | Hardgrove, Sheila | Jones, Phil | Condition 2 | 87% | +12 |
| +17 | 91% | 3901587258 | Hardgrove, Sheila | Jones, Phil | Condition 3 | 87% | +12 |
| +17 | 91% | 3901587258 | Hardgrove, Sheila | Jones, Phil | Condition 4 | 87% | +12 |
| +17 | 91% | 3901587258 | Hardgrove, Sheila | Jones, Phil | Condition 5 | 87% | +12 |

REAL-TIME TIME SERIES MATRIX PATHOPHYSIOLOGIC PATTERN PROCESSOR AND QUALITY ASSESSMENT METHOD

CROSS-REFERENCE TO RELATED APPLICATIONS

This application is a continuation-in-part of U.S. patent application Ser. No. 13/677,291, filed Nov. 14, 2012, which claims the benefit of U.S. Provisional Patent Application No. 61/629,164 filed Nov. 14, 2011 and of U.S. Provisional Patent Application No. 61/629,147 filed Nov. 14, 2011, the disclosures of which are hereby incorporated by reference in their entirety for all purposes. This application is also a continuation-in-part of U.S. patent application Ser. No. 12/437,417 filed May 7, 2009, which claims the benefit of U.S. Provisional Patent No. 61/200,162 filed Nov. 25, 2008 and U.S. Provisional Patent No. 61/126,906 filed May 7, 2008, the disclosures of which are hereby incorporated by reference in their entirety for all purposes. This application is also a continuation-in part of U.S. patent application Ser. No. 12/437,385 filed May 7, 2009, which claims the benefit of U.S. Provisional Patent No. 61/200,162 filed Nov. 25, 2008 and U.S. Provisional Patent No. 61/126,906 filed May 7, 2008, the disclosures of which are hereby incorporated by reference in their entirety for all purposes.

BACKGROUND AND SUMMARY

Conventional scientific principles of detection of conditions, and particularly clinical conditions, have been traditionally based on the determination of a correlativity metric which relates the results of a test to the relative probability of the existence of a condition. Examples of correlativity metrics are sensitivity, specificity, positive predictive value, negative predictive value, and correlation coefficient, among others. Physicians generally use these correlativity metric values with the perception that the actual probability of the condition is reasonably Bayesian and subject to the standard formula from which they may estimate the probability of a condition given a test result using known formulae. Unfortunately, to use these formulae, physicians make general assumptions about the pretest probability (the prior) of the condition.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements may have similar reference numerals. Data, names, and examples are from fictional patients for illustrative purposes. In the following examples and discussion, a number of correlativity metrics relating to probability assessment are shown including specificity, among others.

FIG. 16 is a scenario chart associated with the Event and the associated dependencies depicted in FIG. 15; FIG. 18 is a scenario chart associated with the Binary and the associated dependencies depicted in FIG. 17; FIG. 20 is a scenario chart associated with the Classification and the associated dependencies depicted in FIG. 19; FIG. 22 is a scenario chart associated with the Image and the associated dependencies depicted in FIG. 21; FIG. 24 is a depiction of one embodiment of a snapshot report which can be delivered to a healthcare worker as a report that summarizes top ranking conditions and deltas; FIG. 30 shows a search result for the condition Sepsis within a real-time healthcare environment in which results are patients ranked by Specificity to Sepsis; and FIG. 31 shows a GUI providing filtering by physician and ranking by Specificity; and FIG. 32 shows a GUI providing filtering by physician and ranking by Potential; and FIG. 33 shows a GUI providing filtering by department and ranking by the change in Potential within the last 28 hours.

DETAILED DESCRIPTION PRESENT EMBODIMENTS

Figure 1:
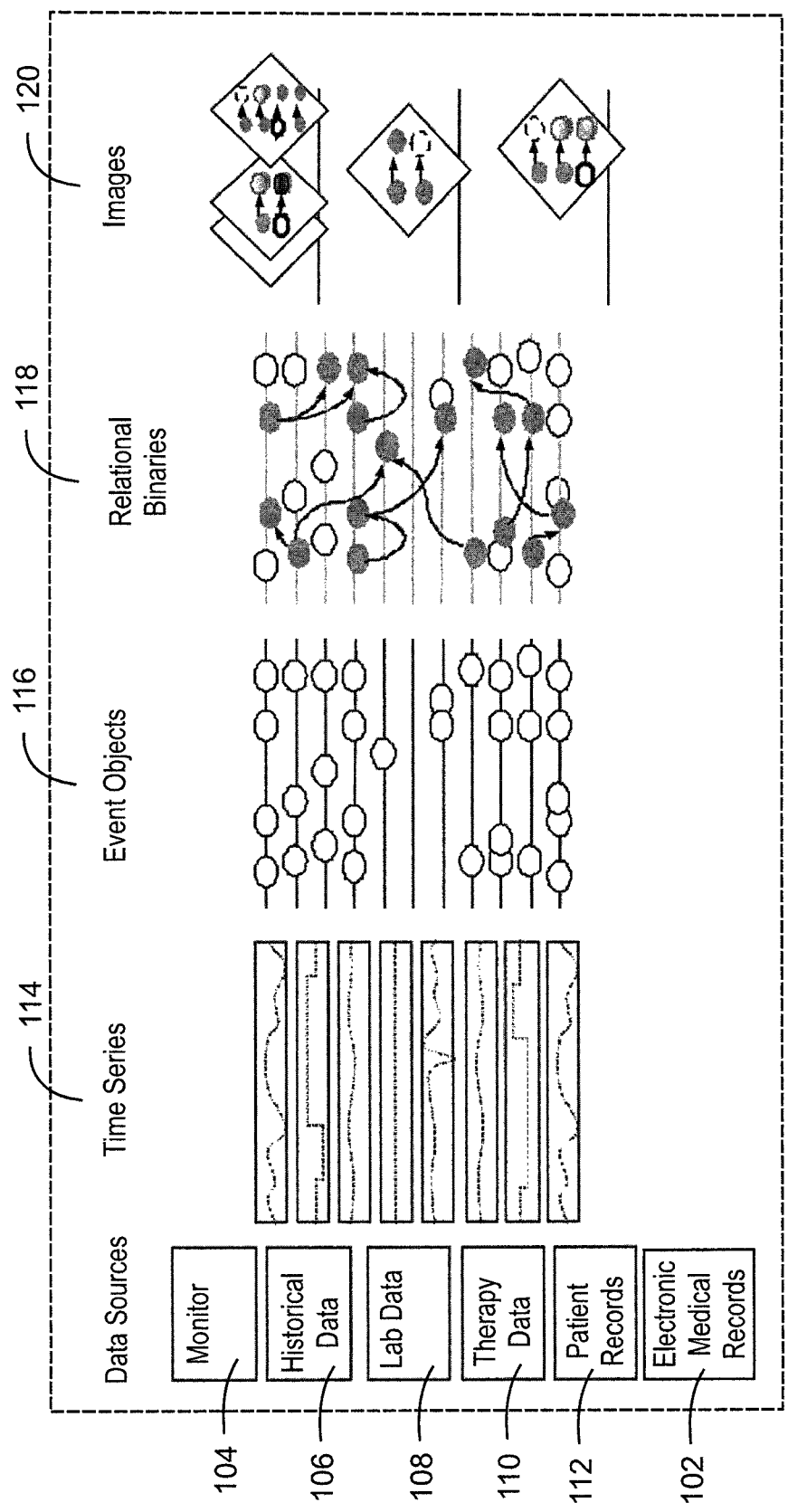
FIG. 1 is a diagram depicting the levels of analysis in accordance with an exemplary embodiment of time series objectification.

When evaluating a patient in a hospital, there are several approaches to define the pretest probability. However, the approaches to define the pretest probability are not reliably effective when applied across a hospital system by different physicians in the evaluation of individual patients to determine the posterior probabilities of complex and dynamic conditions. One such method of defining pretest probability comprises the substitution of prevalence for pretest probability. In some example, the prevalence is derived from the target condition within a population studied in a large clinical trial and/or a meta-analysis of many clinical trials. Deriving the prevalence from the target condition within a population may be unreliable because of the difficulty in verifying that the population of the clinical trials contained sufficient representation of the complex and relational pathophysiology, genetic composition, and/or physiologic vulnerabilities of the instant patient under the physician's care. To accommodate, physicians tend to use the prevalence data from clinical trials as a reference point and then consider previous experiences that are relevant to the perceived significance of other features of the available data and then mentally adjust or calibrate the pretest probability based on these subjective factors before making a final expert guess as to the posterior probability of the condition. In this approach, physicians are considering Bayesian concepts rather than formally calculating the posterior probability. In many instances, this approach may be superior to more rigorous mathematical Bayesian inference methods for determining posterior probability because of the uncontrollable sensitivity this formula exhibit to calculations.

While individual expert physicians may perform well using this subjective approach, the complexity of the variations of human pathophysiology, the variation of populations, the different levels of experience of different physician, as well as many other poorly defined variations, make these "expert" approaches are poorly applicable to large hospital systems because they produce unpredictable results. Worse, confidences in this approach by the experts may mislead care during complex dynamic conditions.

Like the Bayesian approach, the frequentist method of determining posterior probability has been difficult to apply in clinical medicine. This is in part due to the lack of large number of available random trials and the difficulty in comparing complex clinical populations and of achieving true randomization. Because of the limitations of implementation of frequency based posterior probability in clinical medicine, the aforementioned Bayesian approaches have been widely used for this purpose.

In an example, a patient presents to an emergency room with a subcutaneous injury of the knee which demonstrates surrounding inflammation. He has an oral temperature of 100 degrees and the physician orders a Complete Blood Count (CBC) and this returns a white blood cell count (WBC) 8,000/ml. (normal) with a slightly elevated neutrophil count (ANC). The WBC, ANC, and the temperature (alone or in combination) are relatively sensitive tests for sepsis when the results of large clinical trials are considered. In severe sepsis (as with fatal necrotizing fasciitis) the WBC (and ANC) first rises, peaks, and then falls as sepsis progresses toward death so that along this progression timeline (which is highly variable) any value of WBC may be present in severe sepsis depending on the timing of the testing in relation to the progression of the sepsis. The emergency room physician may perceive that the WBC is a sensitive test for sepsis in a population of patients presenting to the emergency room and that a normal WBC is strong evidence that the patients does not have dangerous sepsis. While both perceptions may be true and well supported by clinical trials, they are also highly misleading.

The techniques disclosed in the aforementioned applications provide analysis of patterns and fragments of patterns within both real time and retrospective data sets. The patterns allow researchers to look both forward and backward in time with respect to the patient timeline.

According of one aspect of the present techniques, the trajectory of the sensitivity-specificity relationship point of a test result, variation, pattern, image or other feature of data may be mapped on receiver operating space to indicate its relative position in receiver operating space over time relative to the time/and/or stage of the condition as the dynamic condition progresses. This movement of position of the point in receiver operating space may be provided as a function of time, clinical stage, and/or in relation to another value, variation, pattern or other feature or component of the data.

In an example, the position of a value of WBC of 8,000 in receiver operating space, (as the space relates to the diagnosis of sepsis) moves as sepsis progresses. According to one aspect of the present techniques the relative utility (or value) of an input or output (for example a test, value, variation, pattern, image, or other feature) is determined by analysis and or quantification of its movement and or of at least one aspect of its trajectory in receiver operating space over time, over stage and/or over a range of iterative combination with other inputs or outputs.

Unfortunately the application of conventional quality indicators is similarly flawed. The timeliness of detection, identification, and treatment of conditions such as medical failures are major factors which define the quality and cost of medical care. This is true whether the medical failure (also referred to herein as a distress condition) is clinical failure such as sepsis, or a treatment failure such as a failed response to an antibiotic, or a medication complication, such as heparin induced thrombocytopenia, or a resource utilization failure wherein excessive testing and treatment was applied. Because the quantification and characterization of medical failure is so complex, hospitals use proxies to define quality. In a sense these proxies are "tests results" (testing for quality or efficiency) and one could generate receiver operating curves around them which, for example, provide sensitivity and specificity relationships of the proxy for poor quality. However, these proxies do not characterize or quantify the complexity so that such calculated output may be severely misleading. It is not surprising that such methods are often discounted by physicians as oversimplified. For example, using conventional quality assessment systems the process of attributing poor care or excessively expensive care to a given healthcare worker, hospital or ward, is complicated by the mix of dynamic relational complexities of the conditions of the patients before receiving care, the mix of actions and timeliness of others, the mix of relational responses of the patients, and the mix general misfortunes (or good fortunes) which can occur solely as a function of probabilities, among others. Some of these factors may be out of the control of the healthcare worker or hospital under scrutiny but may affect the proxy and the relative posterior probability estimated using the proxy.

One embodiment of the present techniques comprises a correlativity processor which detects and/or identifies diagnostic patterns in archived data sets and defines a plurality of feature sets of the diagnostic patterns. The diagnostic patterns (also referred to herein as patterns) can include data related to any suitable number of physiological systems or pathophysiologic systems. In some embodiments, the patterns can include time-series related to any suitable number of physiological systems. The processor further determines at least one correlativity (also referred to herein as a correlation) metric of at least one feature set to at least one condition or distress condition occurring in temporal and/or spatial relationship. The processor calculates or otherwise determines a correlativity value indicative of the relationship between the condition and the feature set of the diagnostic pattern. The processor is further programmed to detect and/or identify a target data pattern having at least one similar or otherwise analogous feature set to the diagnostic pattern and to output the correlativity value indicating the relationship of the diagnostic pattern to the condition upon the detection of the target pattern.

In one embodiment correlativity is determined and output as a function of time and/or outputted in real-time or near real time. The correlativity metric values may be outputted to healthcare workers as a function of time. One correlativity metric may be defined by patterns from some suitable portion of the relevant data set in comparison with the outcomes of patients with similar time data patterns of the relevant data set. The correlativity may also be defined by the processor as function of data factors, for example, the integrity of the data, the amount of data, the age of the data, the number and types of relational data streams, the granularity of the data, among others. One embodiment provides processing and providing an output of a correlativity metric responsive to dynamic conditions wherein the metric is recalculated when any values of the global dataset for any set of conditions changes. These changes may comprise, for example; changes in the condition, the occurrence of new conditions or other variables, and changes in the data set, among others. One embodiment provides processing such that the values and relationship between the correlativity of fragments of a data set, and further may provide processing such that the correlativity of the data set is improved as a function of the processing to generate data patterns and/or by automatically ordering additional data based on the patterns. According to one embodiment a change in correlativity is processed to generate a plurality of correlativity components. Each component may be related to a change in at least one of the data set itself or the clinical outputs or care of the patient. In an example, a first correlativity component may be derived from a change in the number of data streams, a second correlativity component may be derived from a change in the duration of the processed data stream, and a third component may be derived from a first clinical change in the patient and a fourth component may be derived from a second clinical change in the patient among others. One embodiment parses the components of dynamic correlativity metrics to objectively determine which additional tests should be ordered given a new pattern.

One embodiment of the present techniques comprises a system and method for processing a plurality of relational parameters and for generating real-time or near real-time correlativity for complex conditions. In one embodiment, the system provides outputting and/or processing those values to provide the user with a real-time or near real-time indication of correlativity for a condition or a plurality of conditions over time for example in a time formatted display such as a time-series. The system may further comprise an alarm processor responsive to at least one feature of the correlativity values. The one feature may comprise, for example, a single, multiple and/or relational value, trend, slope, pattern, derivative, and/or mathematical function, among others. The system may further provide an output indicating the potential correlativity which may be achieved by the addition of a change in the data factors and of calculating and outputting the difference between the actual correlativity and the potential correlativity and/or outputting or automatically correcting the data gap responsible for the difference. In one embodiment, a plurality of time-series of correlativity values or potential correlativity values may be generated and processed to detect the relationships between the time series. In one embodiment, the relationships of these time series patterns may be detected and identified using time series objectification pattern analysis technologies as discussed in U.S. Pat. No. 7,081,095, U.S. Pat. No. 7,758,503, and U.S. patent application Ser. No. 13/102,307, the entire contents of each of which are incorporated by reference as if completely disclosed herein. If preferred, another pattern detection processing method may be used. The software elements and patterns of this application are described further in U.S. patent application Ser. No. 13/677,288, filed Nov. 14, 2012, entitled "Iterative Time Series Matrix Pattern Enhancer Processor," which is incorporated by reference herein in its entirety for all purposes.

In one embodiment, the probability that any single or grouping of testing parameter values comprise a true positive or false positive test for the condition is determined as a function of data set features, comprising for example, the timed relational pattern of the parameter grouping, the relationship of that timed relational pattern to other timed relational patterns along the clinical timeline, the timed presence or absence of other historical or instant clinical parameters and the relationships of these other clinical parameters to each other as well as to the timed relational patterns. Furthermore, in one embodiment, the correlativity of a give set of data for a target condition may also be adjusted by the processor as a function of the processor defined correlativity for of other conditions which may share correlativity components with the target condition. In an embodiment, the above timed relational patterns and clinical parameters affecting at least one correlativity metric are defined as correlativity elements. These correlativity elements and the relationships within and between these correlativity elements may be defined by the processor. Global correlativity to one or more conditions is then defined as a function of those correlativity elements. In addition the relationships within and between these correlativity elements and the additional clinical parameters may be defined. According to one aspect of the present techniques a variable and dynamic time series of global correlativity is defined as a function of these correlativity elements, of the pattern of the global correlativity itself, and of the relational patterns of other global and/or elemental specificities.

The present techniques comprise systems and methods for generating correlativity elements and/or global correlativity for complex conditions and particularly complex medical conditions. In one embodiment the system analyzes and presents in real-time (or near real-time) how closely a condition matches with a set of conditions being monitored based on a plurality of patterns. In some embodiments the conditions are medical conditions and the patterns are clinical, and/or medical patterns and or healthcare facility care and/or expense patterns in relation to clinical patterns. Some embodiments provide systems and methods for identifying, analyzing and presenting in real-time (or near real-time) how closely a patient's condition matches with a set of conditions being monitored based on a plurality of patterns within the physiologic and medical care data by utilizing comparisons in real-time (or near real-time) to patterns identified in a large representative set of retrospective patient data sets. According to one aspect of an embodiment, the analysis and presentation provides for early detection, identification, quantification, and/or tracking of medical or clinical failure (for example physiologic failure, treatment failure, and medical complications). Another aspect of an embodiment provides early detection, identification, quantification, and/or tracking of medical responses (for example physiologic response and treatment response). Another aspect of an embodiment provides early detection, identification, quantification, and/or tracking of clinical management variations. Another aspect of an embodiment provides early detection, identification, quantification, and/or tracking of healthcare expense variations.

While the analysis of patterns and pattern relationships derived from massive real-time and retrospective data has many advantages, improvements which reduce the complexity of the outputs as well as enhanced methods for correlating complex patterns with conditions or sets of conditions would be beneficial.

According to one aspect of the techniques, the correlation to a condition may be associated with an individual pattern such that within a retrospective set of patients the identification of this pattern corresponds to at least one correlativity metric. The processor may be programmed to identify the pattern as comprising or being otherwise associated with a correlativity value.

According to one embodiment the processor, with or without the help of the user, may create a large number of patterns (e.g. 10,000 patterns) and these patterns may be quantified to generate and/or associate global correlativity values for a set of conditions (e.g. 200 conditions) within a large number of retrospective patient data sets (e.g. 100,000 patient data sets). In one embodiment, this set of patterns can be utilized against other patient sets (either in real-time, near real-time or with retrospective data) to generate a time-series of correlativity values. Alternatively, global and elemental correlativity values can be generated into a time series or other distribution. This set of time-series and/or distributions can be used for a wide range of purposes including visualization, reporting, interfacing with other systems and/or analysis among others. An important advantage of this systems and method is that it provides for the processing of massive data sets with computational transparency, (for example in the time domain) such that the user, who may be a physician or nurse is readily able to understand the patterns which are matched to a given condition.

The present techniques provide a system and method to derive, present, and analyze global and/or elemental correlativity values for selected conditions in real-time or near real-time. The techniques further provide alarm processors responsive to global and/or elemental correlativity with the alarm processor being responsive to substantially the entire data set if desired. For example, the alarm processors may be responsive to massive pattern relationships across hundreds of time series and across extended periods of time to generate global and/or elemental correlativity thresholds, trends, patterns, and/or relationships between correlativity metrics and/or responsive to thresholds, trends, patterns, and/or relationships of global and/or elemental correlativity metrics and other conditions or parameters. In one embodiment the present techniques comprises a patient data processing system programmed to iteratively process a first set of EMR data and/or monitor data to generate a reference set of patterns from patients, the reference set being characterized by one or more known target conditions, derive a reference set of correlativity values for the target condition corresponding to the reference set of patterns, iteratively process a second set of EMR data and/or monitor data to generate an output set of matching patterns which match the patterns relating to the condition, compare that output set of patterns to the reference set of patterns to derive an output set of correlativity values for the condition, and output an indication based on the output set of correlativity values. The processor may be programmed to aggregate and/or persist some suitable number of the partially or completely identified patterns. The matching may be of the type described in the patent applications referenced herein or by another method, and/or may comprise matching in the time domain by temporal matching, spatial matching, component matching, region matching, binary matching, and/or image matching. The processor may apply substantially the same processing method to generate the reference set and the output set. The processor may identify at least one pattern within an interval defined by a predetermined, time, a pattern, and/or a set of data. The processor may identify a value that represents a parameter of the correlativity metric set. In an example, the parameter may be at least one of a maximum value, a mean value, a median value, and/or a value derived from a mathematical formula and/or a value or range of values derived by further processing of the parameter value among others. The processor may generate a value that represents the count or another quantification or parameter of matching patterns relating to at least one correlativity metric, which quantification may be derived from the count of matching patterns within a range of at least one correlativity metric. The processor may generate a value that represents the count of matching patterns within a range of at least one correlativity metric which may for example be specified or dynamically determined according to a parameter of the at least one correlativity metric set (such as the maximum value) of at least one correlativity metric.

In one embodiment, the patient data processing system is programmed to recognize the unavailability, sparseness and/or staleness of data sets to determine a value that represents the potential maximum of at least one correlativity metric if the unavailable, sparse or stale data sets were available, sufficiently sampled and timely as well as identifying the source data stream or streams that generated the potential. One data processing system may be programmed to compare the value of a potential of at least correlativity metric if a data set were complete and or timely, to an existing correlativity value to generate a value of the potential gap.

In one embodiment, the patient data processing system is programmed to process multiple successive windows to produce a time series of values representing values of at least one metric, potential, and or potential gap for a plurality of conditions and/or diagnoses and to present on a monitor or other user interface display in a real time or near real time environment and/or to generate an alarm based on a threshold of the values within one or more of the time series which alarm may be, for example based on a pattern of values within one or more of the time series and/or based on relationships between these time series. In one embodiment the processor is programmed to analyze at least one of the above time series combined with a time series of expense, cost, and/or resource utilization, to analyze, report and monitor the quality and/or efficiency of care within a healthcare facility and/or to indicate a request for or trigger the initiation of additional tests, treatment and/or therapy, for quality assessment, reporting, analysis, dashboard display, search, rank, filter, sort or otherwise distinguish and/or compare patients, windows of times within patients, groups of patients, departments, physicians and/or healthcare facilities training, and/or interface into other systems and/or processors. The processor may be programmed to generate other metrics, indices and/or indicators from the above parameters, patterns, specificities, potentials, and/or potential gaps and to determine efficacy and/or cost effectiveness of treatment, therapy and/or bio markers. In one example the processor may be programmed to apply the potential and/or potential gap to determine correctable delay in relation to diagnosis and/or condition identification/specification. The processor may be programmed to apply the delay, cost, or another metric or indicators to determine and output the rank, and/or to sort, or otherwise provide distinguishing output relating to cost efficiency and/or quality and/or timeliness of healthcare workers, departments, and/or facilities.

In one embodiment the processor is programmed to generate and/or persist the primary or relational reference and target patterns and/or the primary or relational patterns of at least one correlativity metric, potential and potential gap described in for successive windows of time as for display on a user interface for a specified point in time. The display may be configured to indicate or demonstrate change over time as in a single diagram using time as an axis or by use of an animation or looping animation and may provide a catalog of patterns that can be searched, sorted, filtered or otherwise navigated. The display or other output may provide a visualization in which a parameter of at least one correlativity metric and a parameter of the potential and/or a parameter of the potential gap are shown together. The parameter of the at least one correlativity metric may be the maximum value of the metric. The visualization may provide a maximum correlativity and the count of related patterns, shown together. The change in any of the above values, parameters, and relationships may be shown for a given time span as, for example graphically and/or by animation. The processor may utilize the patient data processing system of claim 1 in which the underlying definition and/or abstractions of the patterns used can be altered in real time or near real time. The processor may be programmed to cluster, characterize and/or differentiate patients and patient groups, to compare patterns, specificities, potential, potential gap, and or other processor outputs against healthcare worker notes or other mechanisms of specifying the existence of a condition and/or diagnosis. The processor may be programmed to use a time series of at least one correlativity metric to a condition to alter, annotate or otherwise enhance the time series of at least one correlativity metric to another condition and/or the points within that time series.

In one embodiment the processor is programmed to provide a visualization of patient data which is suggested, limited, ranked, sorted, tagged, highlighted, emphasized, annotated, colored, distinguished or otherwise enhanced by the data generated from the above processing. In ranking may be based on a parameter value of at least one correlativity metric, a count of the number of matching patterns, and or a combination of the value and the count, and/or the severity of the patterns or by another method. The visualizations may be presented together with a representation of cost or a cost time series and/or with underlying definition and/or abstractions used to identify patterns are displayed.

In one embodiment, the processor may be programmed to determine and report potentially beneficial tests, and/or testing frequency, adverse lab conditions, and/or to order a change in testing such as additional testing and/or order a change in the frequency of resting based on the values and/or patterns of at least one metric, potential and/or potential gap.

In one embodiment, the reference set may be derived from a group of retrospective patients and the patterns identified may be updated to improve the quality and/or robustness of the output as new patients are added to the group. In one embodiment the processing system adds new patients to the group from additional sets processed as for example a target set processed in a real time or a near real time environment. The system may programmed such that patients diagnosed by a definitive test, by another indication, or otherwise marked with a condition are added to the retrospective set of patients.

In one embodiment, the processor analyzes a set of patterns to determine the effectiveness of the set of patterns with regard to generating responsive and robust time series of at least one correlativity metric to a given set of conditions. The processor may utilize a patient data processing system in which the underlying definition and/or abstractions of the patterns used can be altered in real time or near real time.

In one embodiment, the output of the processor or derivatives of the processor disclosed herein are used to develop new or improved medical products such as devices, biomarkers, tests, and treatments or determining the efficacy of existing medical products by comparing at least one of the outputs of the processor disclosed herein prior to the addition of the medical device to the outputs after the inclusion of the medical device to detect at least one favorable effect such as for example, an increase in a correlativity metric, a reduction in potential gap, a reduction in cost, a reduction in resource utilization, a more rapid rise in at least one correlativity metric over time, a relational benefit. In one embodiment the processor or derivatives of the processor disclosed herein determine the adverse effects of medical products such as devices, biomarkers, tests, and treatments by comparing at least one of the outputs of the processor disclosed herein prior to the addition of the medical device to the outputs after the inclusion of the medical device to detect at least one adverse effect such as for example, a decrease in a correlativity metric, an increase in potential gap, an increase in cost, an increase in resource utilization, a slower rise (or a fall) in at least one correlativity metric over time, a relational adverse effect. In one embodiment the processor is programmed to separate the favorable effect(s) from the adverse effect(s) and to compare the favorable effect(s) to the adverse effect(s).

For purposes of summarizing the disclosure, certain aspects, advantages and features of the techniques have been described herein. The techniques disclosed herein can be embodied or carried out in a manner that achieves or enhances one advantage or group of advantages as taught herein without necessarily achieving other advantages as can be taught or suggested herein.

As shown in FIG. 1, electronic medical records (EMR) data 102, medical monitor data 104, historical data 106, lab data 108, therapy data 110, patient records 112 and other data sources can be converted into time series data 114. The time series data 114 can be analyzed to identify patterns of various levels of complexity (e.g. event objects 116, relational binaries 118, and/or images 120). Various methods to perform these processes are discussed in detail in the aforementioned patents and applications.

In one embodiment, patterns may be described with various mechanisms that abstract elements of the pattern and encapsulate them into a data structure that describes a class of patterns. In one embodiment, this encapsulation is called Occurrence Type. An Occurrence Type includes sufficient information to search for the pattern within the time series or other time formatted data set derived from the patient and or other data. An Occurrence Type can be constructed in various ways including, for example, using sets of parameters, sets of Boolean rules, sets of equations, sets of instructions, a software element, or a script of a textual Domain Specific Language (DSL), a diagram or model of a visual DSL among others.

Regardless of the internals of the Occurrence Type, one function of the Occurrence Type is to identify instances of a specified physiological pattern within a region of the time series data. In the present embodiment, a Region is defined as a set of physiological signals and a start and end time. A Region may be a portion of the time series data for a single patient, a subset of time series data for a patient or a set of data that crosses multiple patients.

An Occurrence Type can be applied to a Region to derive occurrence instances (simply called Occurrences) of the pattern described within the Occurrence Type. (In the present embodiment, the mechanism for accomplishing this may be the Patient Safety Processor engine describe in the aforementioned applications.) If an Occurrence Type is applied to a Region and one or more Occurrence defined by the Type is found then the Region may be said to be positive for the Occurrence Type. Regions may be either positive or negative for an Occurrence Type.

This binary specificity provides the ability to compare the predictive power of an Occurrence Type against a known "gold standard" to determine whether the occurrence type is True Positive (TP), False Positive (FP), True Negative (TN) or False Negative (FN). For example, if a Researcher or the processor has designated a Region as having a particular condition (e.g. a disease state such as Sepsis) then the application of an Occurrence Type to the Region may result in one of the four outcomes described above—TP, FP, TN, FN.

In one embodiment, a set of regions may be designated as a Target Region Universe. Within this Target Region Universe a subset of regions may be designated as to be "known" to have a condition (e.g. Sepsis). This subset may be designated as the Known Region Set. A Target Region Universe with a Known Region Set may be designated as a Marked Region Universe.

Once the Target Region Universe and the Known Region Set have been identified (as, for example, through a tagging mechanism) the result of the application of an Occurrence Type to the regions in the Target Region Universe can be compared against these sets to determine the correlativity metric (such as Sensitivity, Specificity, Positive Predictive Value, Negative Predictive Value, Likelihood Ratios among others) of the Occurrence Type to the condition being considered (the Target Condition).

Occurrence Types may represent a correlativity metric or a set of correlativity metrics for a Target Condition. For example, a single Occurrence Type may represent a Sensitivity/Specificity pair and a set of Occurrence Types represents a set of Sensitivity/Specificity pairs.

In one embodiment, Specificity is used as the primary correlativity metric. In an alternative embodiment, a Positive Predictive Value is used as a primary correlativity metric. In one embodiment, the Specificity of Occurrence Types may be applied such that a repository of patterns and time series matrices, which may be objectified (derived from a large set of retrospective patient data) that contains a wide range of Occurrence Types with a high degree of granularity of Specificity and a significant coverage within the possible ranges of Specificity may be used by a real-time monitor to produce a time-series of Specificity toward a given condition.

Figure 2:
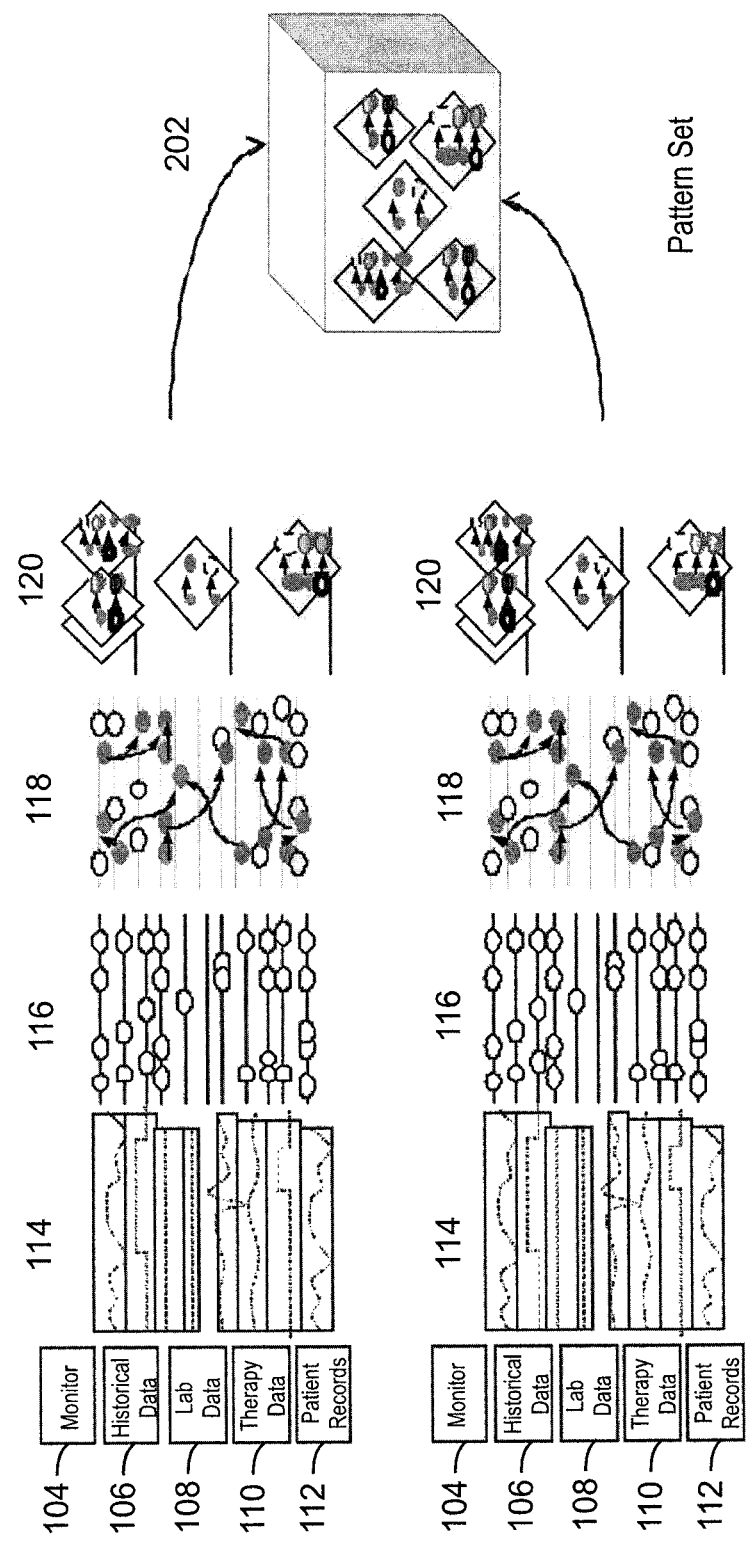
FIG. 2 is a diagram depicting the generation of a pattern set from a set of retrospective data sets.

In an embodiment, a Real-Time Specificity Monitor may be split into a plurality of separate processes. A first process may be to create a Specificity marked pattern set 302 (FIGS. 2 and 3) from a pattern set 202 and a reference patient set 304 and a second process may be to use that Specificity marked pattern set 302 in a real-time environment to produce a set of Specificity time-series 402 of FIG. 4 that may provide a wide range of capabilities including display of specificity as a time-series, pattern recognition within specificity streams, real-time alarming, real-time reporting, condition ranking within and among patients, specificity dashboards, early disease identification, and identification of potentially unreported conditions among others. In one embodiment these two phases noted above are separated in time and may be executed in two separate and/or disparate environments. The creation of the Specificity marked pattern set 302 may be accomplished, for example, at a research facility. The results may be distilled, synthesized and may be persisted into a reduced and/or single data structure (e.g. a set of database tables or a single file). The Specificity marked pattern set 302 then may be the output of the first phase and an input of phase two.

One embodiment is configured so that continuous improvement can be accomplished within the Specificity marked pattern set 302. Additionally refined sets can be provided subsequently to the real-time environment from the research facility or other sources. For example, larger and larger sets of retrospective patient data sets can be applied to provide greater verification of the Specificity values. Using the present techniques, researchers can continue to discover better patterns or increase coverage and layering within the set. Pattern and/or Specificity refinements can be submitted then to the real-time environment.

One Embodiment of a Method and Process for Creating a Specificity Marked Pattern Set 302

One embodiment of a real-time specificity monitor (RSM) uses a specificity marked pattern set 302 to generate multiple time series of specificity in real-time or with any suitable delay. The specificity marked pattern set 302 may be created as a separate process executed prior to the use of the RSM.

An alternative embodiment uses a Positive Predictive Value. Alternatively, multiple correlativity metrics are calculated and maintained simultaneously.

In one embodiment, the Specificity marked pattern set 302 may be composed of a set of patterns encapsulated as Occurrence Types combined with a set of Specificity values where each pattern may have one Specificity value for each monitored condition. For example, if the RSM monitors Sepsis, Sleep Apnea and Congestive Heart Failure conditions, then each pattern within the Specificity marked pattern set 302 will have 3 Specificity values attached to them (e.g. through a foreign-key relationship in a relational database)—one for Sepsis, one for Sleep Apnea and one for Congestive Heart Failure. Alternatively, Specificity values may be excluded if they are below a threshold indicating "No Correlation".

Figure 3:
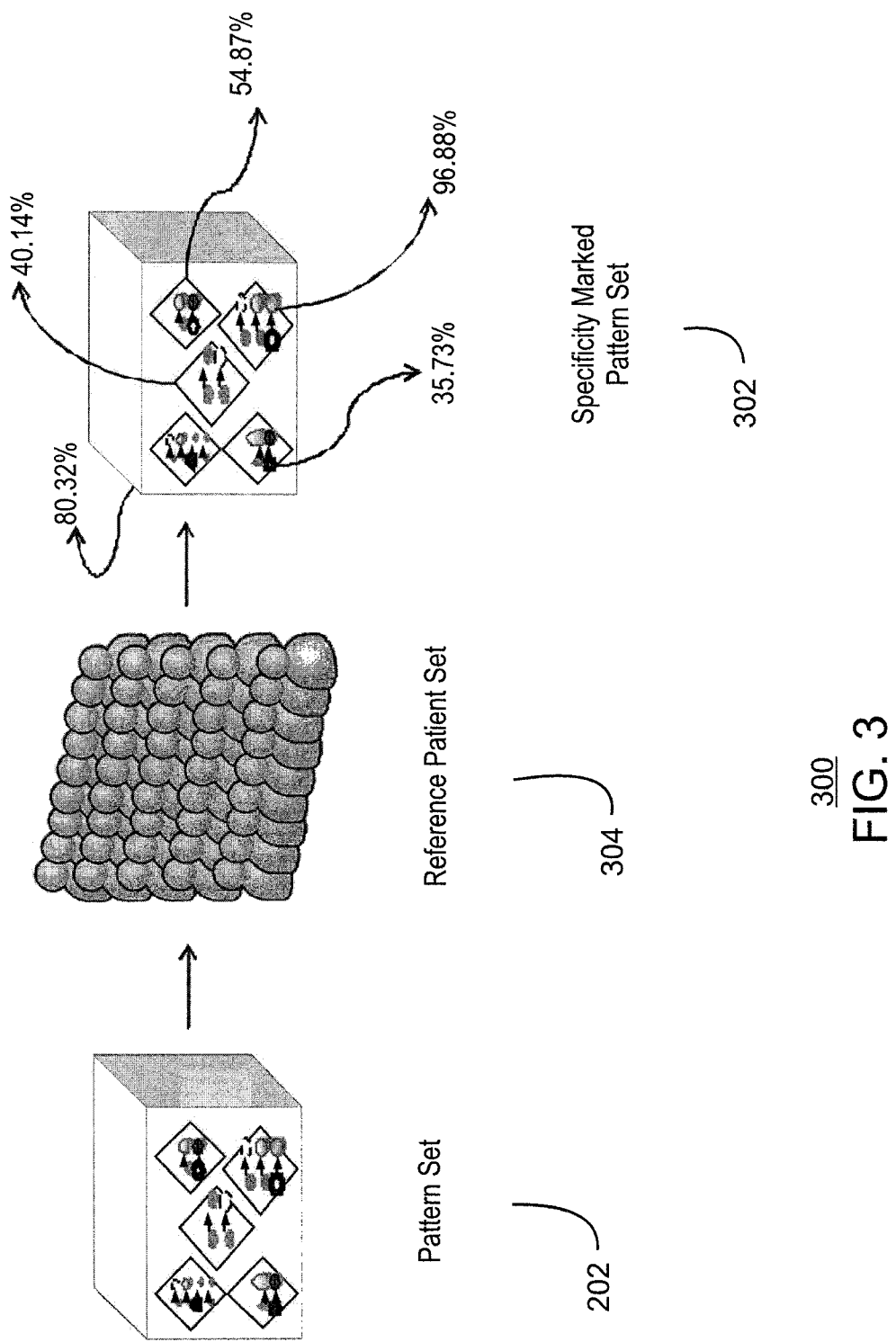
FIG. 3 is a diagram showing how a Pattern Set is marked with Specificity through analysis against a Reference Patient Set.
Figure 4:
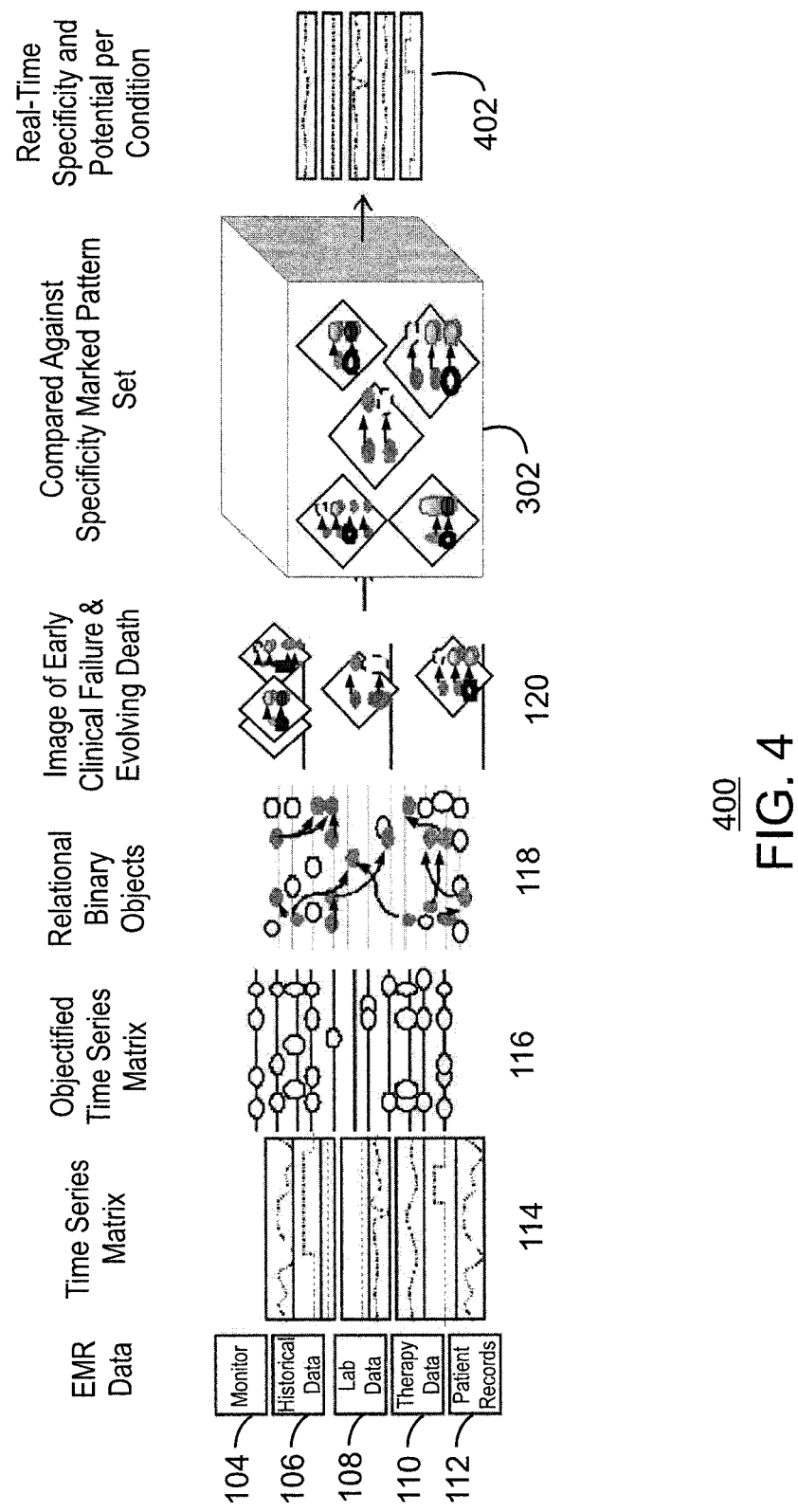
FIG. 4 is an expansion of the diagram in FIG. 1 depicting how, during a real time execution of objectification occurrences can be compared with the Marked Pattern Set to generate time series of Specificity and Potential.

A specificity marked pattern set 302 may represent the combination of a pattern set 302 with specificity values found by executing the patterns against a reference patient set 304 (see FIG. 3). For example, a specificity marked pattern set 302 may be derived from any pattern set 202 and a reference patient set 304. Any pattern set (e.g. a group of 1 or more patterns) may be used to create a specificity marked pattern set 302. In some example, multiple Reference Patient Sets 304 may be used to create multiple Specificity marked pattern set 302s 302.

Pattern sets 202 may come from many different sources. For example, pattern sets 202 may be created by researchers or the creation of pattern sets 202 can be automated either completely or in a way directed by a researcher. In one embodiment, pattern sets 202 can be created with any suitable combination of detecting predetermined pattern sets 202 and automating the creation of pattern sets 202.

In one embodiment, a pattern set 202 may be generated from an automated process which uses a Marked Region Universe, a set of Occurrence Types supplied by the researcher and a set of parameters to direct the generation of patterns. This process may be called Iterative Pattern Enhancement (also referred to herein as IPE).

An effective Specificity marked pattern set 302 preferably has important characteristics including High Coverage, Robustness and Verified Predictability.

A Set with High Coverage will cover a wide range of specificity values for each condition. In one embodiment, coverage may be important at various levels of Specificity. Alternatively, Specificity values below a certain value are not stored. The maximum Specificity value stored represents the maximum value that the RSM can indicate. In some embodiments, coverage at the high end of specificity (i.e. approaching 100%) is one of many sets of value. Value may be added by increasing the granularity of coverage at various specificity levels. Increased granularity supports effective identification of specificity trends.

According to one embodiment the processor quantifies Robustness of the data. In an example Robustness may be represented by layered coverage. In particular, layered coverage where the patterns represented target different signal sets and/or identify separate manifestations of a disease state. For example, since inflammation is one early relationship indicator of Sepsis it may be advantageous for the Pattern Set 202 to include multiple indicators of inflammation using different physiological signals (e.g. WBC and Temperature) as well as multiple patterns within those sets (e.g. Thresholds and Trends). Including patterns with different physiological signal set dependencies increases the likelihood that useful patterns will be found in real-time. This means that patterns that address a particular perturbation or other manifestation may warrant inclusion even if they identify the condition with a lower Specificity.

Further, the goal of Robustness suggests the inclusion of pattern elements as well as whole patterns. For example, if a drop in Bicarbonate is found to have a Specificity of 64% to Sepsis and a drop in Platelets is found to have a Specificity of 56% to Sepsis and the relationship of a drop in Bicarbonate preceding a drop in Platelets is found to have a Specificity of 71% to Sepsis then according to one aspect of the present techniques the principle of Robustness suggests including the relationship pattern (which has the highest Specificity) and also the individual elements. In this way, the initial drop in Bicarbonate will register with the RSM as 64% to Sepsis and then when a drop in Platelets occurs the RSM will show the movement to 71% to Sepsis. In patterns with a large set of sub-elements the inclusion of the sub-elements provides a high degree of responsiveness to changes in Specificity.

Finally, in one embodiment, a Pattern Set 202 may be tested for its predictability against Patient Reference Sets other than the set from which it was constructed and/or originally used to derive Specificity. Variability in Specificity may be expected between Reference Sets but wide swings in variability can indicate patterns that were "over-tuned" to a particular Reference Set. Verification using multiple Patient Reference Sets can identify and eliminate patterns based on anomalous data features rather than elements that accurately represent physiological phenomenon associated with conditions. Researcher oversight, along with verification of predictability against multiple Patient Reference Sets increases the effectiveness of the RSM.

Once the Specificity marked pattern set 302 has been created it can be persisted in various ways including within a relational database, in a data file or set of files, encapsulated within an executable file, or as a serialized stream among others.

One Embodiment of a Method and Process for Generating Real-Time Specificity Time Series Given a Specificity marked pattern set 302 the Real-Time Specificity Monitor (RSM) may generate a set of time series for each patient in real-time (or near real-time) which can be queried, displayed and analyzed.

In one embodiment, occurrence types are encapsulated using a software element. A software element, as referred to herein, can include computer instructions written using any suitable human-readable computer language. For example, the occurrence types can be encapsulated using a Domain-Specific Language (DSL) called Pattern Definition Language (PDL). In some embodiments, occurrence types can contain PDL Scripts that describe a class of patterns from which pattern instances can be identified. Alternatively, other methods for defining occurrence types may be employed.

Figure 5:
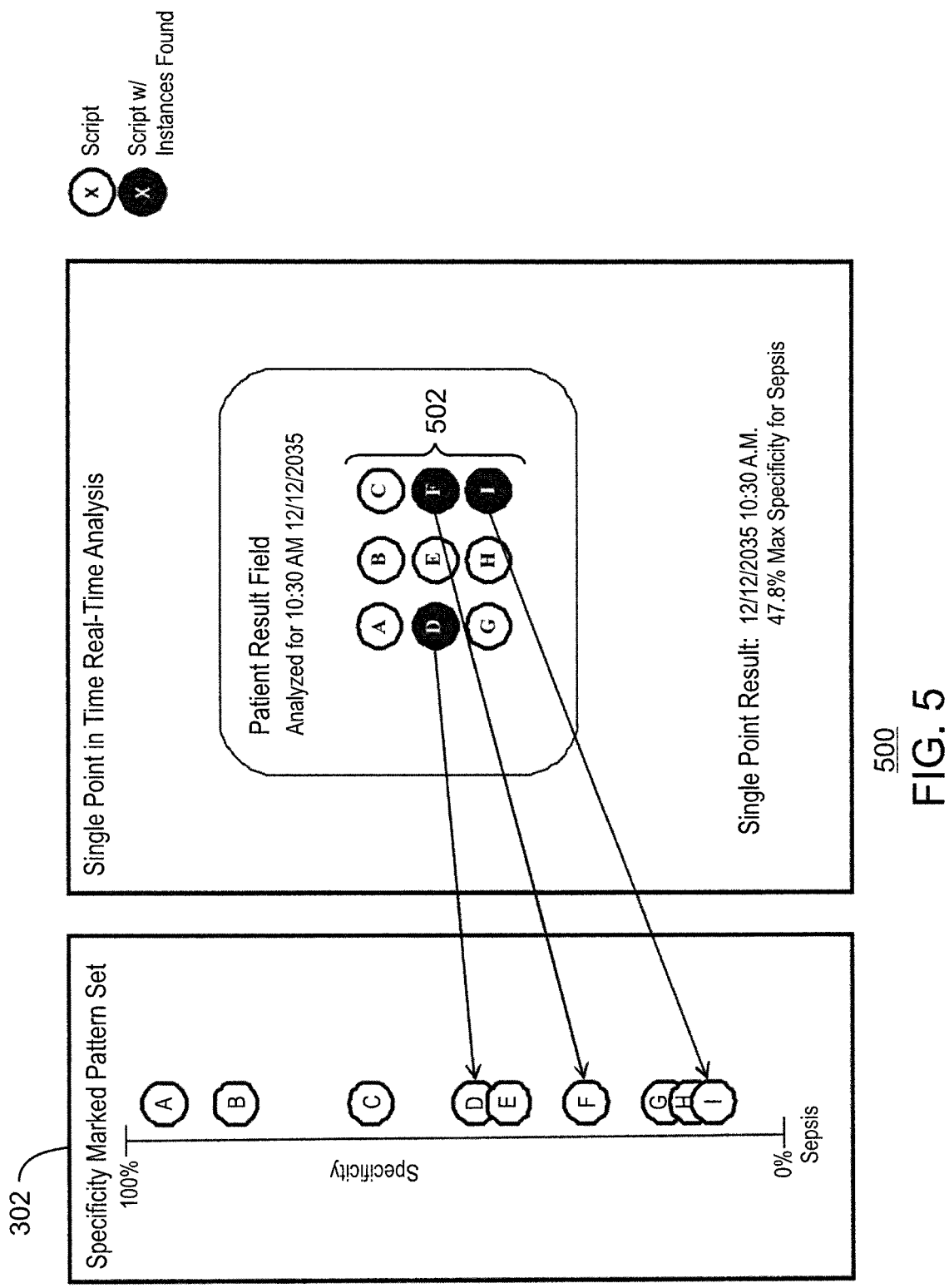
FIG. 5 depicts one embodiment of an acquisition of a single point of Specificity to Sepsis.

At any given point in time in a patient stay the RSM may execute the acquisition of a single point of Specificity. FIG. 5 illustrates the acquisition of a single point of specificity to sepsis. In this case 9 software elements 502 are shown (labeled A through I) for the purpose of illustration. These 9 software elements 502 are encapsulated in a specificity marked pattern set 302 and are shown here sorted by the software element's values of specificity related to sepsis. In the example illustrated in FIG. 5, at a particular time, such as 10:30 AM 12/12/2035, the data for a single patient that has been collected up to that time are analyzed using the 9 software elements 502 and the results are placed into the Patient Results Field 504. Each software element 502 may be marked as Negative or Positive as described above (i.e. according to the ability to identify 1 or more instances of the pattern defined). In one embodiment, once the software elements 502 have been executed and the results determined the Positive Software elements 502 are aggregated and linked back to the Specificity values marked in the Specificity marked pattern set 302. Finally, the maximum Specificity may be determined (Software element D—48.8%) and becomes the value in a time-value pair (12/12/2035 10:30, 48.8) which represents a single point in the Sepsis Specificity time series for this patient.

Figure 6:
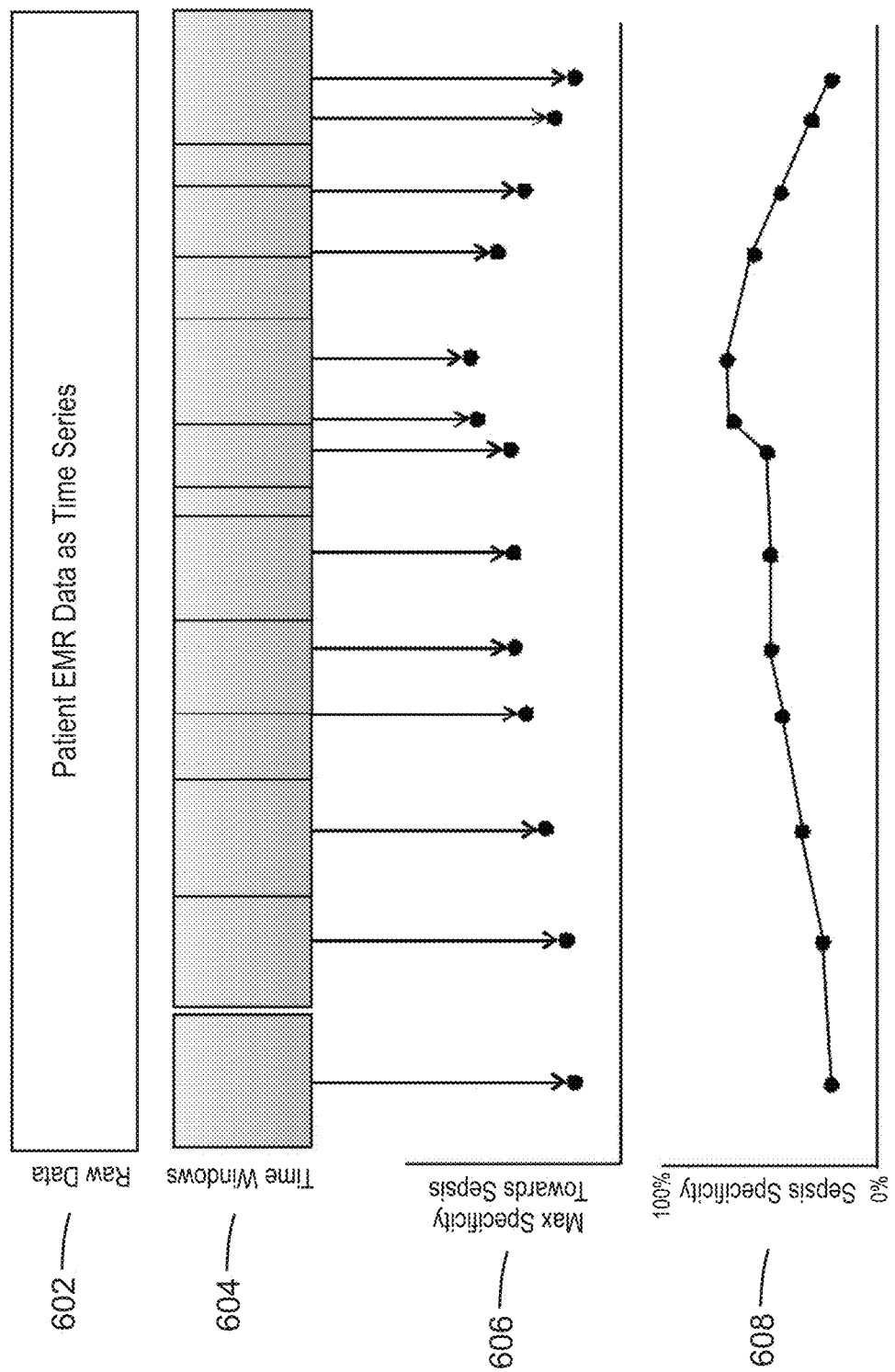
FIG. 6 is a diagram showing the flow from raw data to a time series of Specificity by using a sliding window technique.

This process can be repeated for additional points in time to create a time series of Specificity towards Sepsis. In one embodiment, a time-series may be created by generating a value for every point in time for which any new values have been added to the patient data stream. In an alternative embodiment, a sampling process can be employed using a sliding window approach (as shown in FIG. 6). As shown patient data (also referred to herein as raw data) 602 may be broken up into regions of data 604 (with fixed or variable time horizons and either fixed or variable sizes) and each window generates a single point of Specificity per condition 606. The aggregation of these points creates a Sepsis Specificity time series for this patient 608. A time series of Specificity can be generated as shown in FIG. 6 for either real-time, delayed data, or retrospective data.

In the present embodiment, the windowing mechanism may be driven by three parameters: Offset, Window Size and Condition within Span. The Offset may be the distance between start times of the windows and may be fixed (e.g. sampling) or dynamic (e.g. based on incoming data). The Window Size may be the size of the time span of the window within which to search. This value may also be fixed or based on data (such as the condition being referenced). The Condition within Span may be the maximum time allowed between the final found instance end time and the window end time. The addition of the "Condition within Span" allows the window size to be large enough to identify long-evolving patterns without forcing a long delay before the time series responds to data that indicates the patient is moving away from a condition. Due to the fact that the maximum Specificity is used, the inclusion of the Condition within Span avoids incurring a delay of the entire window size before negative movement can occur in the Specificity time series.

Figure 7:
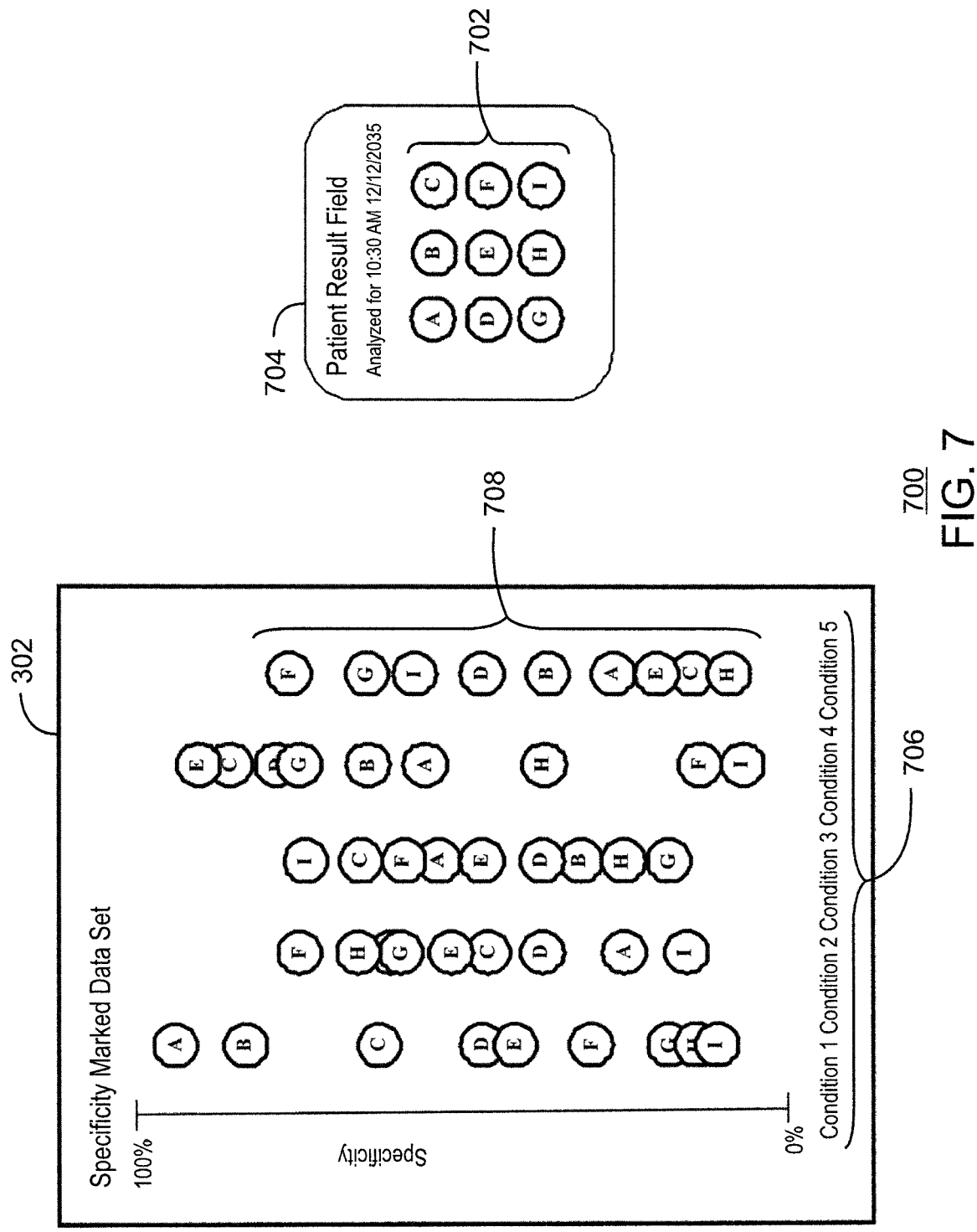
FIG. 7 depicts the setup for an example of the process called Simultaneous Multi-Condition Analysis.

In the present embodiment, Simultaneous Multi-Condition Analysis may be employed as one way to enhance the acquisition of the real-time Specificity time series. In the present embodiment, Simultaneous Multi-Condition Analysis begins with a Specificity marked pattern set 302 in which the patterns 702 are marked with specificity for some suitable number of conditions. As shown in FIG. 7, an example is illustrated with 9 patterns 702 (labeled A through I) in a patient result field 704 marked for 5 conditions 706. The patterns 702 are duplicated per condition and sorted by Specificity to produce 5 columns of patterns each column sorted by Specificity to the condition for the column. In the present embodiment, the columns are called the Specificity Stack 708 for a condition 706 (e.g. the sepsis specificity stack, among others). Any suitable number of patterns 702 can be in each specificity stack 708.

Figure 8:
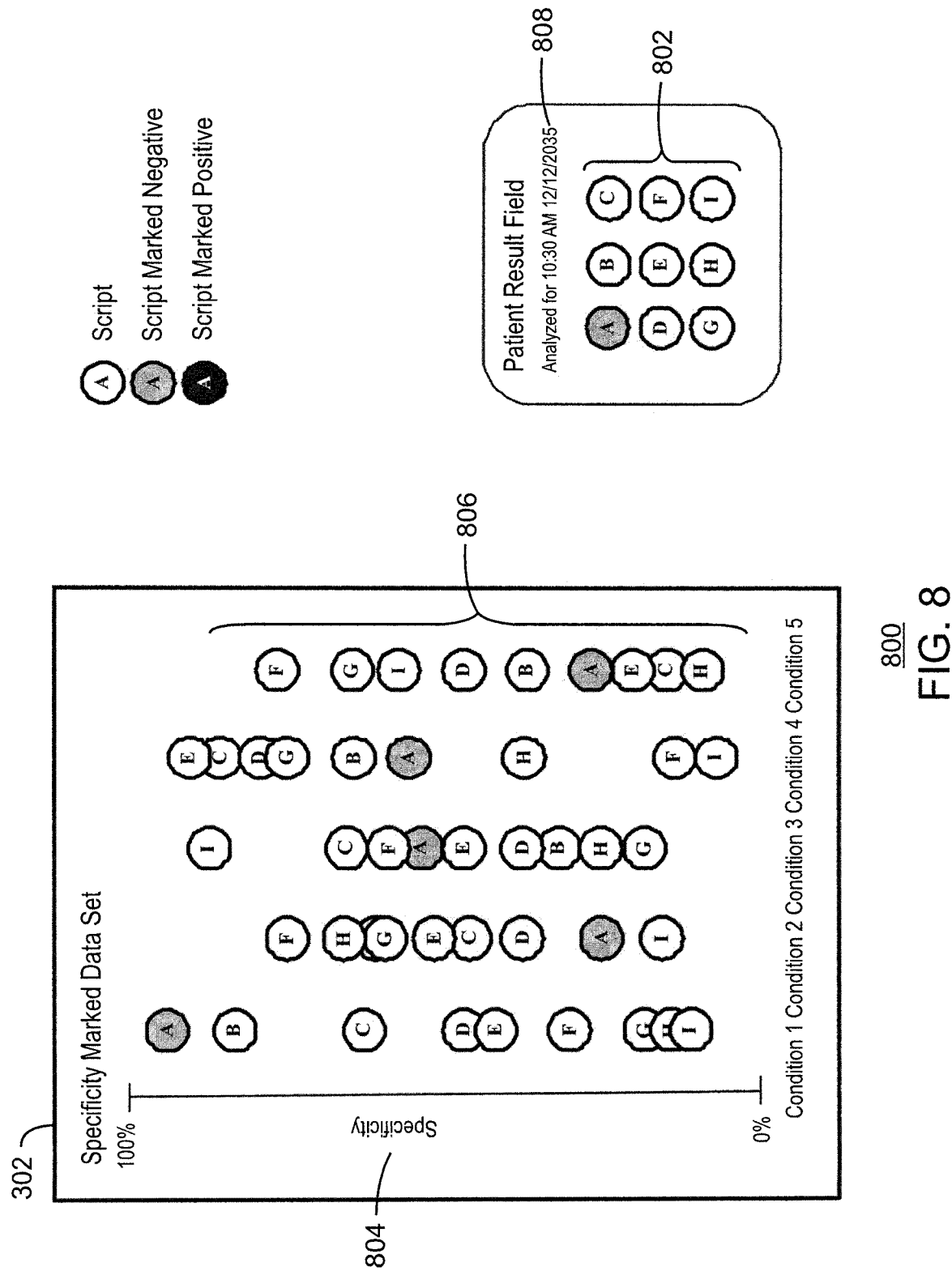
FIG. 8 depicts the first step in a 7 step example of the process called Simultaneous Multi-Condition Analysis.

FIG. 8 illustrates an example in which simultaneous multi-condition analysis begins with the selection of a Software element 802 that has a highest specificity 804 the specificity stacks 806. High Specificity software elements 802 are chosen because the goal of the algorithm is to identify the maximum specificity 806 within each specificity stack 806. By starting at the top (i.e. the highest specificity 804) some software elements 802 can be excluded from execution. Once we find a software element 802 that is positive, the software elements 802 below the positive software element 802 can be eliminated. In the illustrated example of FIG. 8, Software element A is determined to be a positive software element. In some embodiments, the algorithm may use other rules and/or queries to determine the first/next Software element 802 to select. For example, the total Specificity 804 across the specificity stacks 806 could be used (e.g. by selecting the maximum). As shown in FIG. 8, the selected software element 802 (Software element A) may be then executed and/or evaluated to determine if the selected software element 802 is positive. In some examples, Software element A can be found to be negative for the patient for the time window 808 ending at 10:30 AM 12/12/2035 and therefore Software element A may be marked negative across the specificity stacks 806.

Figure 9:
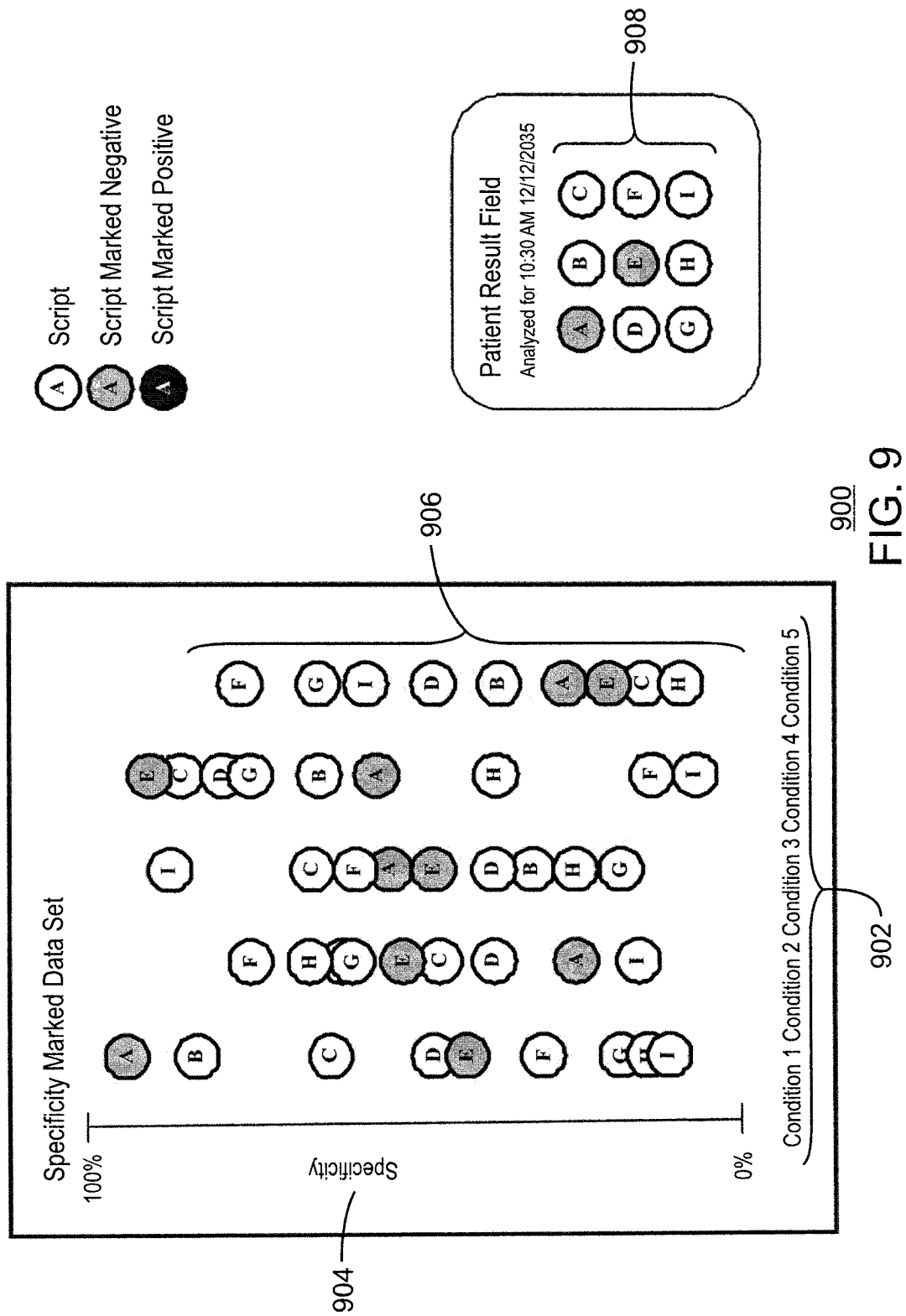
FIG. 9 depicts the second step in a 7 step example of the process called Simultaneous Multi-Condition Analysis.
Figure 10:
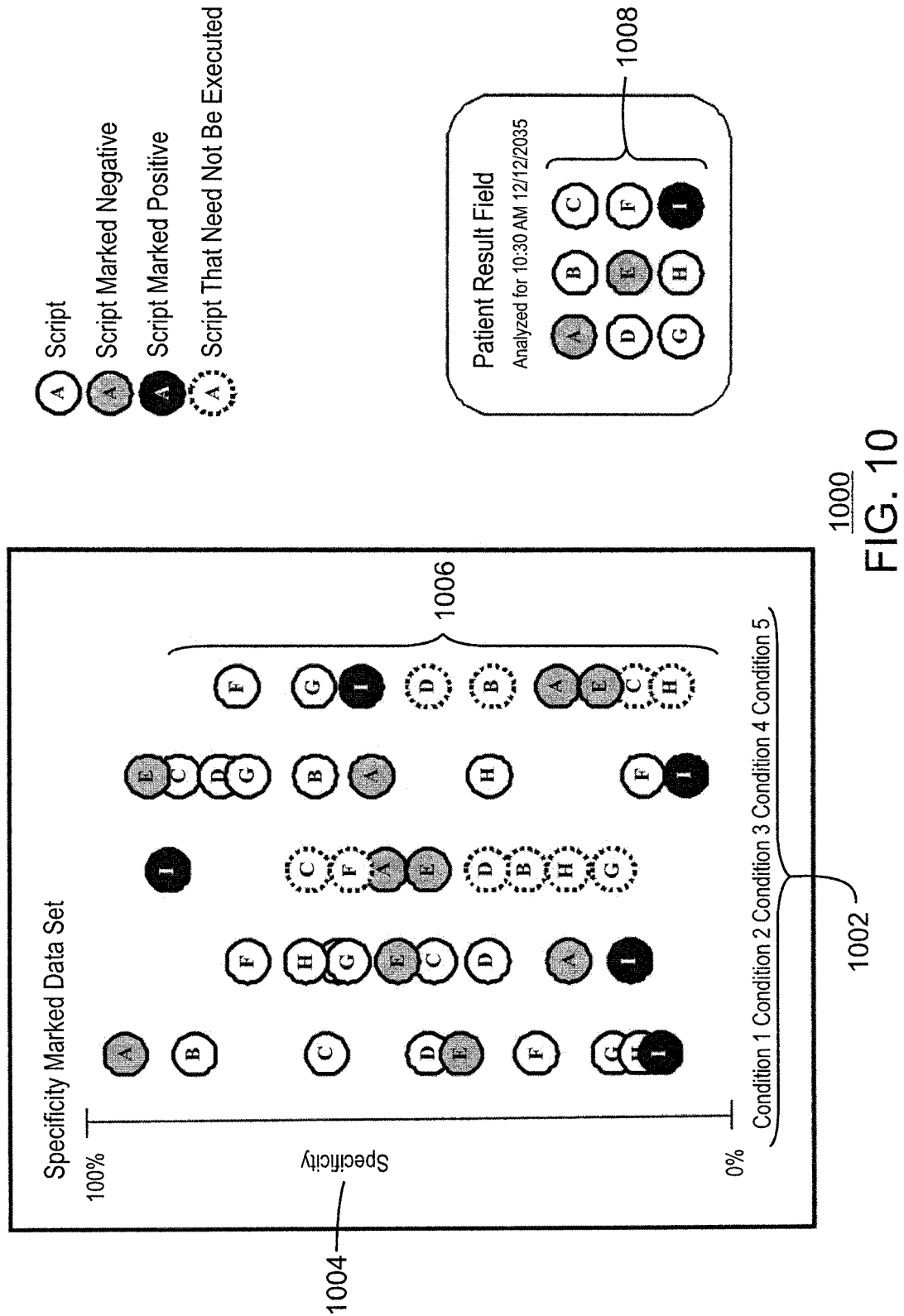
FIG. 10 depicts the third step in a 7 step example of the process called Simultaneous Multi-Condition Analysis.
Figure 11:
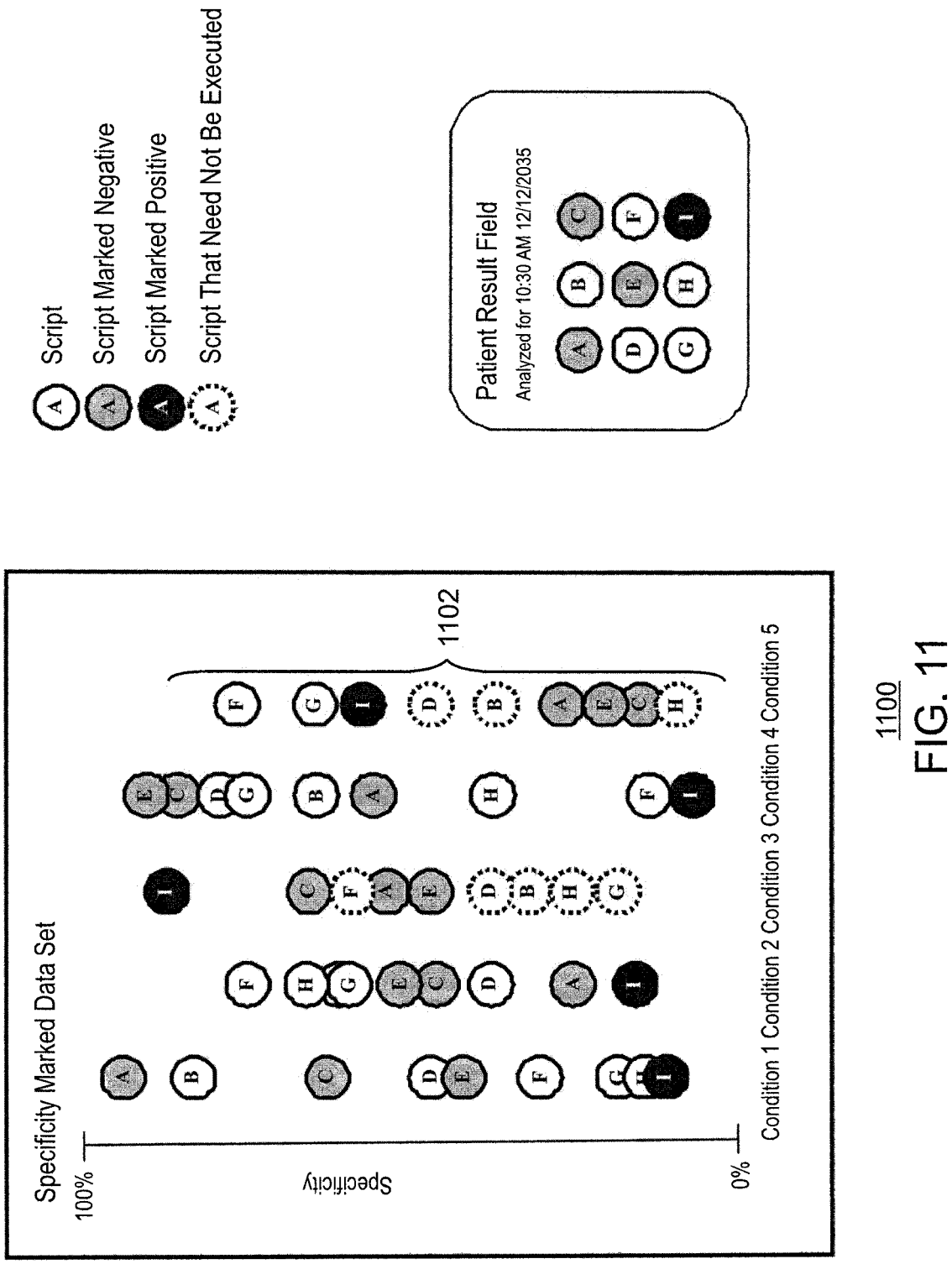
FIG. 11 depicts the fourth step in a 7 step example of the process called Simultaneous Multi-Condition Analysis.
Figure 12:
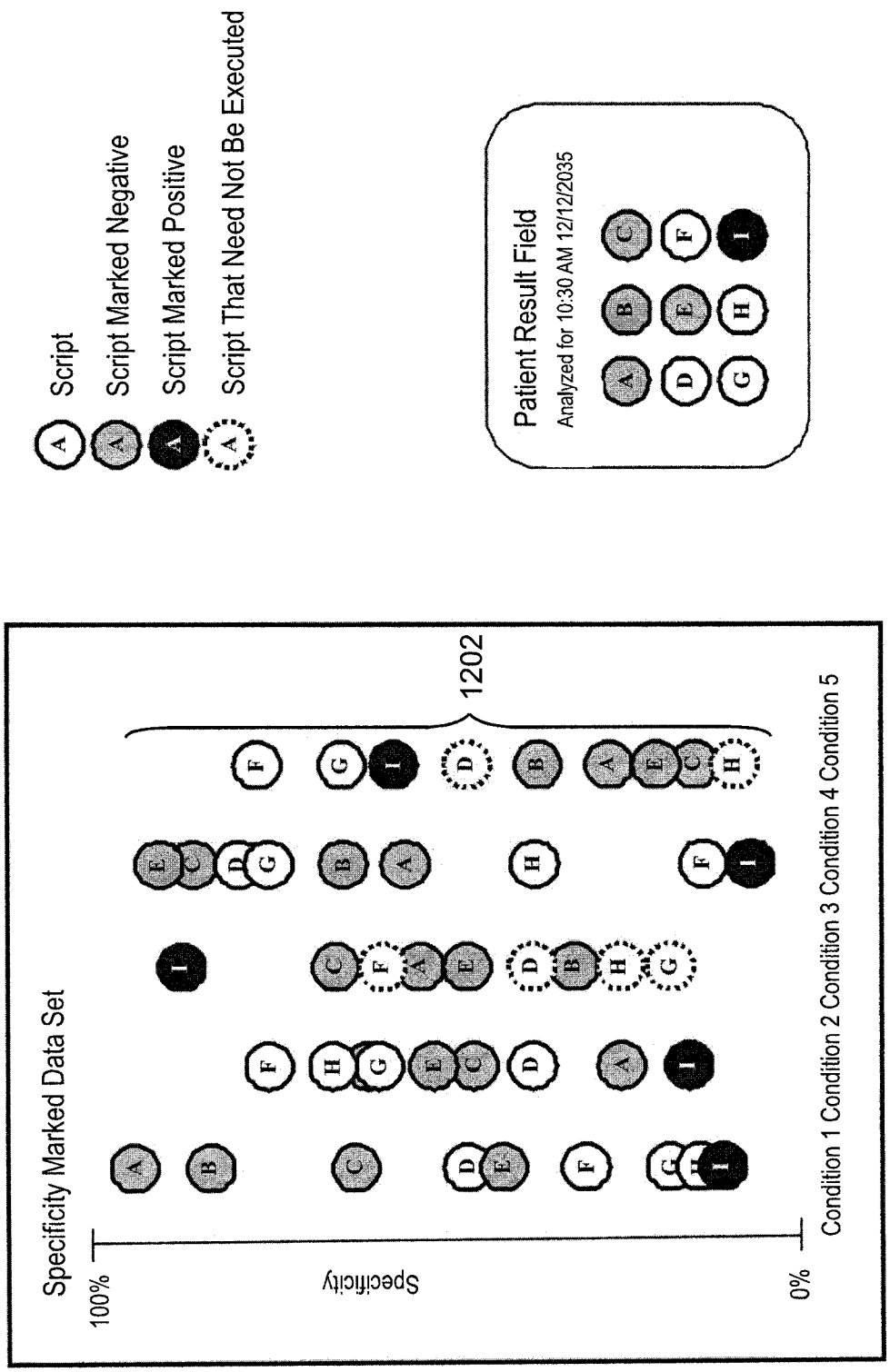
FIG. 12 depicts the fifth step in a 7 step example of the process called Simultaneous Multi-Condition Analysis.
Figure 13:
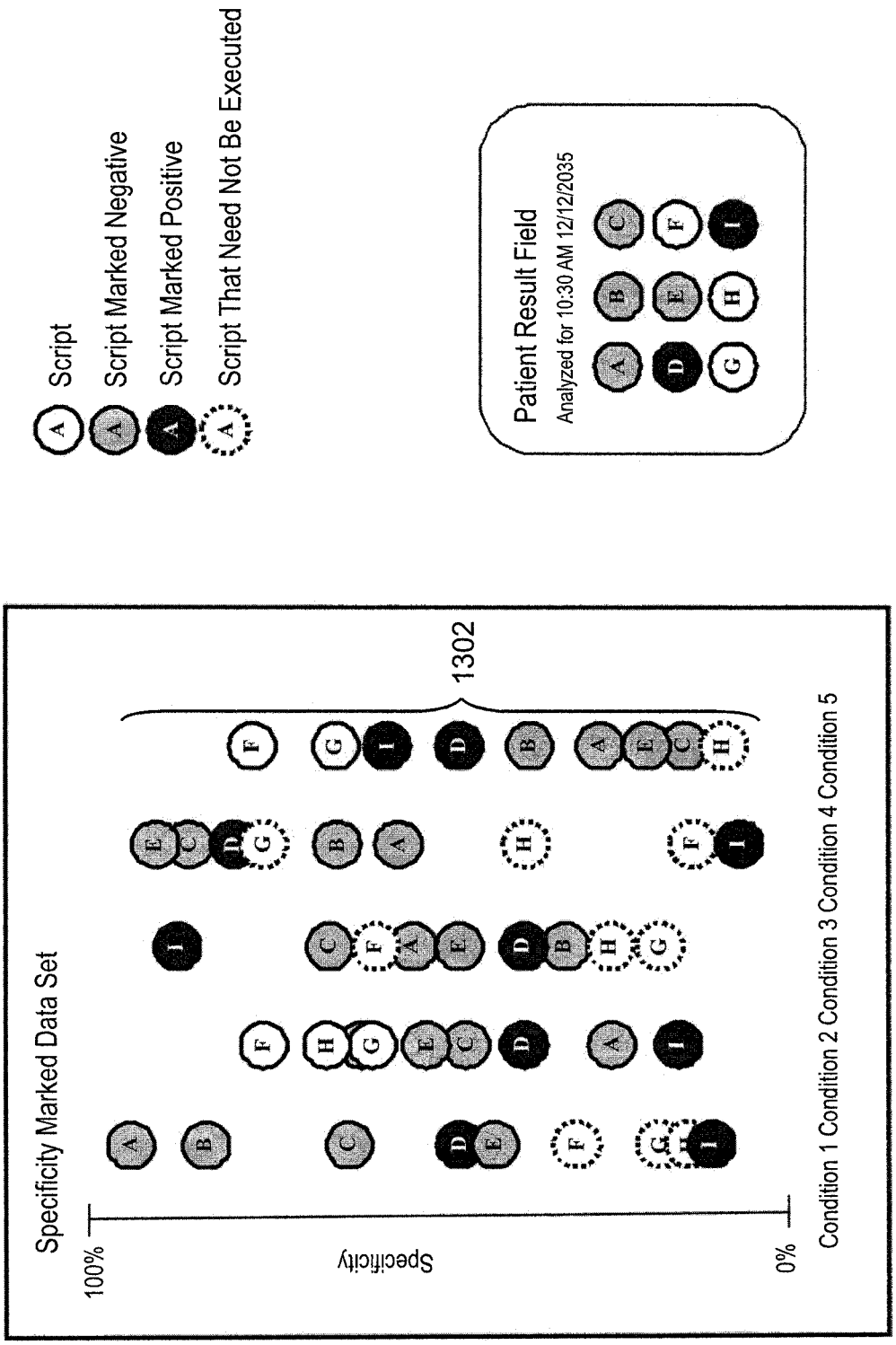
FIG. 13 depicts the sixth step in a 7 step example of the process called Simultaneous Multi-Condition Analysis.
Figure 14:
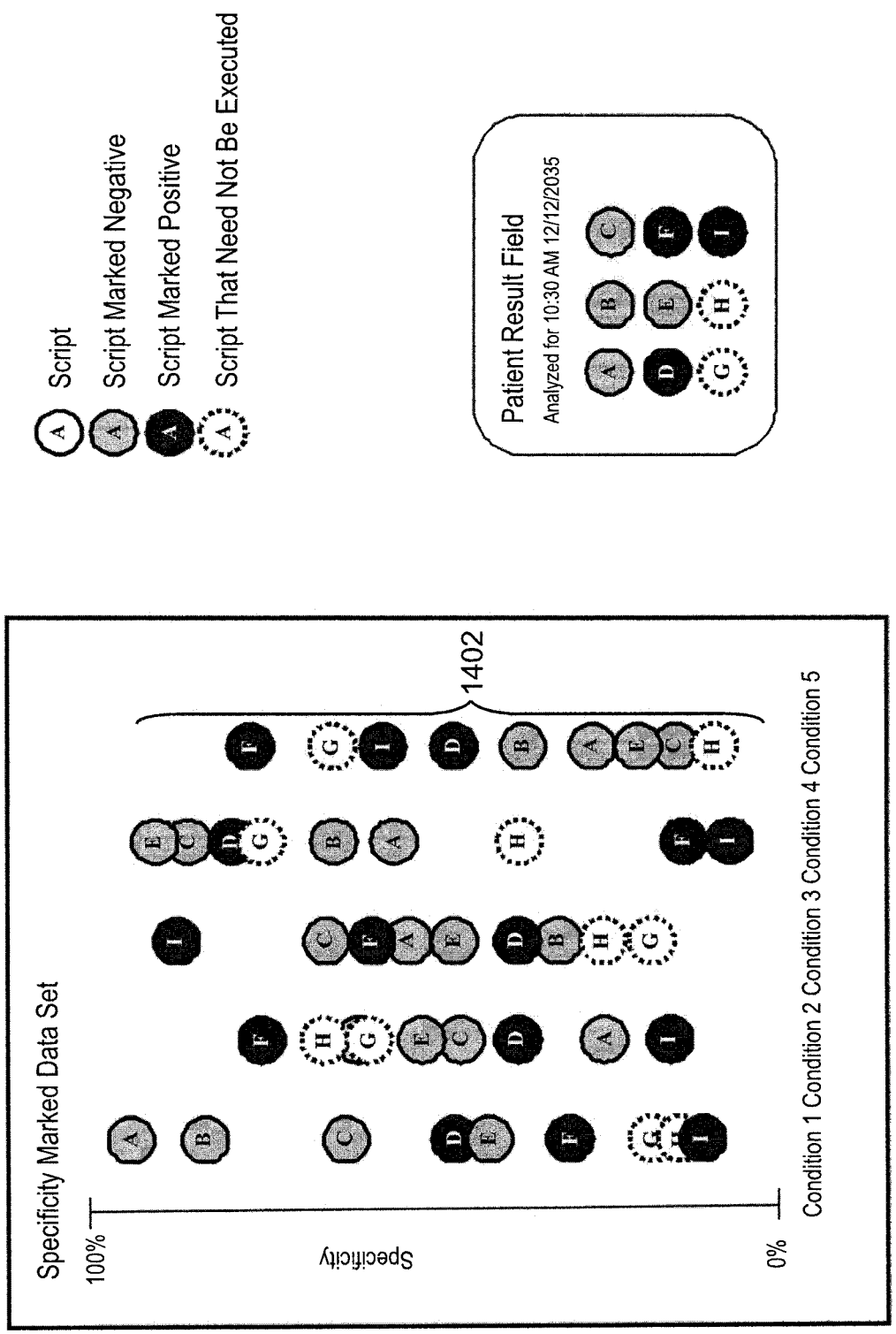
FIG. 14 depicts the last step in a 7 step example of the process called Simultaneous Multi-Condition Analysis.

In some examples, the next Software element 802 to be selected may be software element E (indicated by the circled E) and, in this example, software element E is executed and shown to be negative. The results of executing an addition software element, such as software element E, are shown in FIG. 9. The results of FIG. 9 can include any suitable number of conditions 902, any suitable number of specificity values 904, and any suitable number of specificity stacks 906 that correspond with software elements 908. In some embodiments, a third Software element can be selected, such as Software element I, and after execution the software element I can be shown to be positive. The results of executing an additional software element, such as Software Element I, are shown in FIG. 10. In some embodiments, the results can include any suitable number of conditions 1002, any suitable number of specificity values 1004, and any suitable number of specificity stacks 1006 that correspond with software elements 1008. In one embodiment, the RSM calculates the maximum Specificity. In the example illustrated in FIG. 10, Software element I is positive, so the Software elements below Software element I in the Specificity Stacks 1006 may not be executed. Further, the maximum specificity 1004 is known for Type I and can be reported. In some embodiments, the next two software elements 1008 to be executed may be software element C and software element B. In the example illustrated in FIG. 11, software element C and software element B may be determined to be negative and therefore software element C and software element B may be marked as negative in the specificity stacks 1102 and 1202 as shown in FIGS. 11 and 12 respectively. In some embodiments, an additional software element, such as software element D, may be executed and found to be positive as indicated in the specificity stack 1302 of FIG. 13. FIG. 14 illustrates an example in which the maximum specificity for sepsis and Type II are known and can be reported. In some embodiments, software element F may be chosen and found to be positive in the specificity stack 1402. In some examples, executing software element F may complete the process of determining the maximum specificity for the conditions, which can be reported. In the example of FIG. 14, the maximum specificity for any suitable number of conditions, such as five conditions, is determined by executing 7 of the 9 software elements. In some examples, partial results (e.g. the results for Type I)

could be obtained early in the process after executing any suitable number of software elements.

One Embodiment of a Method and Process for Generating Confidence Metrics

A time series of Maximum Specificity can provide a powerful tool for early recognition of physiological conditions. Given a high Specificity, a physician or other medical worker knows that patterns that exist in the patient have in the past, in a reference set of patients, correlated to the condition. This information can be a part of the decision-making process of the medical worker in real time. The existence of a high specificity value for a condition indicates the existence of patterns and a positive correlation in the reference set.

A low Specificity, on the other hand, may not reflect the lack of existence of the patterns in question. A low Specificity may indicate either the lack of existence of patterns or the unavailability of data to the RSM. A high Specificity can indicate the availability of data and the identification of patterns within that data. A low Specificity may be the result of either unavailable data or the failure to identify patterns within the available data. In the present embodiment, the RSM provides the ability to differentiate between those two scenarios and to disambiguate the medium or low Specificity values.

The RSM defines the concept of Potential as a supporting value stream to the Maximum Specificity. Potential may be made up of two parts—a value (called the Potential Value) and a set of physiological streams that contribute to the Potential. For example, it can be said that at a particular point in time that a Patient has a 45% Specificity to Sepsis. This means that the maximum Specificity found within the Specificity marked pattern set 302 (as described above) is 45% Y. It may also be said that the same patient at that point in time has a 63% Potential to Sepsis on Platelets and Neutrophils. This means that two physiological signals are unavailable to the RSM—Platelets and Neutrophils. It also means that among the patterns in the Specificity marked pattern set 302 there is at least one pattern with a 63% Specificity to Sepsis that might be identified if Platelets and Neutrophils were available to the RSM. It does not mean that if Platelets and Neutrophils were available that the Specificity would jump to 63%, but that if those streams were available there is a potential to jump to 63% Specificity.

Potential indicates at least two important things—how much Specificity could be gained if unavailable time series were available to the RSM and which time series are unavailable that could contribute that much. In one embodiment the Potential Value cannot be below the Specificity Value. If no patterns are found within the Specificity marked pattern set 302 which could potentially provide a higher Specificity given the addition of unavailable time series then the Potential Value is equal the Specificity Value. The difference between the Potential Value and the Specificity Value may be called the Potential Gap. For example if the Potential is 54% and the Potential is 88% then the Potential Gap is 34% (Potential—Specificity). The Potential gap has a range between 1 and 100 and is reported in % (e.g. "There is a 23% Potential Gap in Sepsis Specificity").

The Potential Gap can be used to automate testing to reduce the Potential Gap. In one embodiment the Potential Gap refers to the specificity definable by routine testing without the addition of expensive and often invasive tests which may have a specificity approaching 100%. For example, a Potential Gap may apply to a sepsis diagnosis with routine EMR and monitoring data sets but may not include the portion of the gap which would be present given a positive blood culture. According to one aspect of the present techniques if the specificity of a data set increases for sepsis and a potential gap is present (for example because certain lab or monitoring data are absent, such as, for example, a hand differential derived band count, a platelet count, a recent bicarbonate value, and/or a respiratory rate among others) then the processor may be programmed to order testing which may close the gap and may be further programmed to provide an alert and/or order blood cultures upon at least one feature of the specificity values derived after the gap has been closed.

Potential gaps can provide information related to the role of indicating a confidence level in the specificity value. If the potential gap is zero, the RSM may be indicating that the patterns within the specificity marked pattern set 302 could provide a higher specificity value and which the processor is programmed to expect to have the routine data they request for their generation but they have not been identified in that data providing a higher confidence that the target condition is not likely.

In the present embodiment, the Potential Value may be calculated with the same granularity as Specificity and therefore provides a time series that "flows" at the same rate and with the same ranges as the Specificity Time Series. In the present embodiment the Potential may be typically displayed along with the Specificity (as described in subsequent sections).

In some embodiments, Potential may be calculated at the same time as Specificity. For example, during Simultaneous Multi-Condition Analysis (described above) Potential may be calculated and considered. As described above, during Simultaneous Multi-Condition Analysis the execution and evaluation of an Occurrence Type (implemented as a Software element in the above example) resulted in a positive or negative result for each software element. If a positive result is found (e.g. one or more of the described patterns are identified within the Region), the associated Specificity Value for the given Condition may be applied as a candidate Maximum Specificity amount. If a negative result is found, there is no effect on Maximum Specificity. In the present embodiment, when Potential is being calculated then the negative result incurs further investigation to determine if the associated Specificity Value can be applied as a candidate Maximum Potential amount. In some embodiments, for each Software element evaluated there are 3 possible results: no effect, the associated Specificity amount applied as a candidate for Maximum Specificity, or the associated Specificity amount applied as a candidate for Maximum Potential.

In some embodiments, patterns are encapsulated within a Domain Specific Language (DSL) called the Pattern Definition Language (PDL). Within the PDL there are categories of Occurrences that represent the morphology of the patterns being described. For example, an Event may be described as a contiguous set of points within a single physiological signal (called a Point Stream) whereas a Binary is the relationship between two other Occurrences in time. In the present embodiment, the method of calculating Potential may be related to the Occurrence Category (i.e. morphology) of the Anchor pattern within the PDL Script.

FIGS. 15-22 provide a wide range of morphologies and corresponding representative scenarios with detailed explanations of how Specificity and Potential are derived.

Figure 15:
FIG. 15 is tightly associated with FIG. 16 and depicts a dependency diagram for an Event.

FIGS. 15 and 16 show scenarios for an Event.

Figure 17:
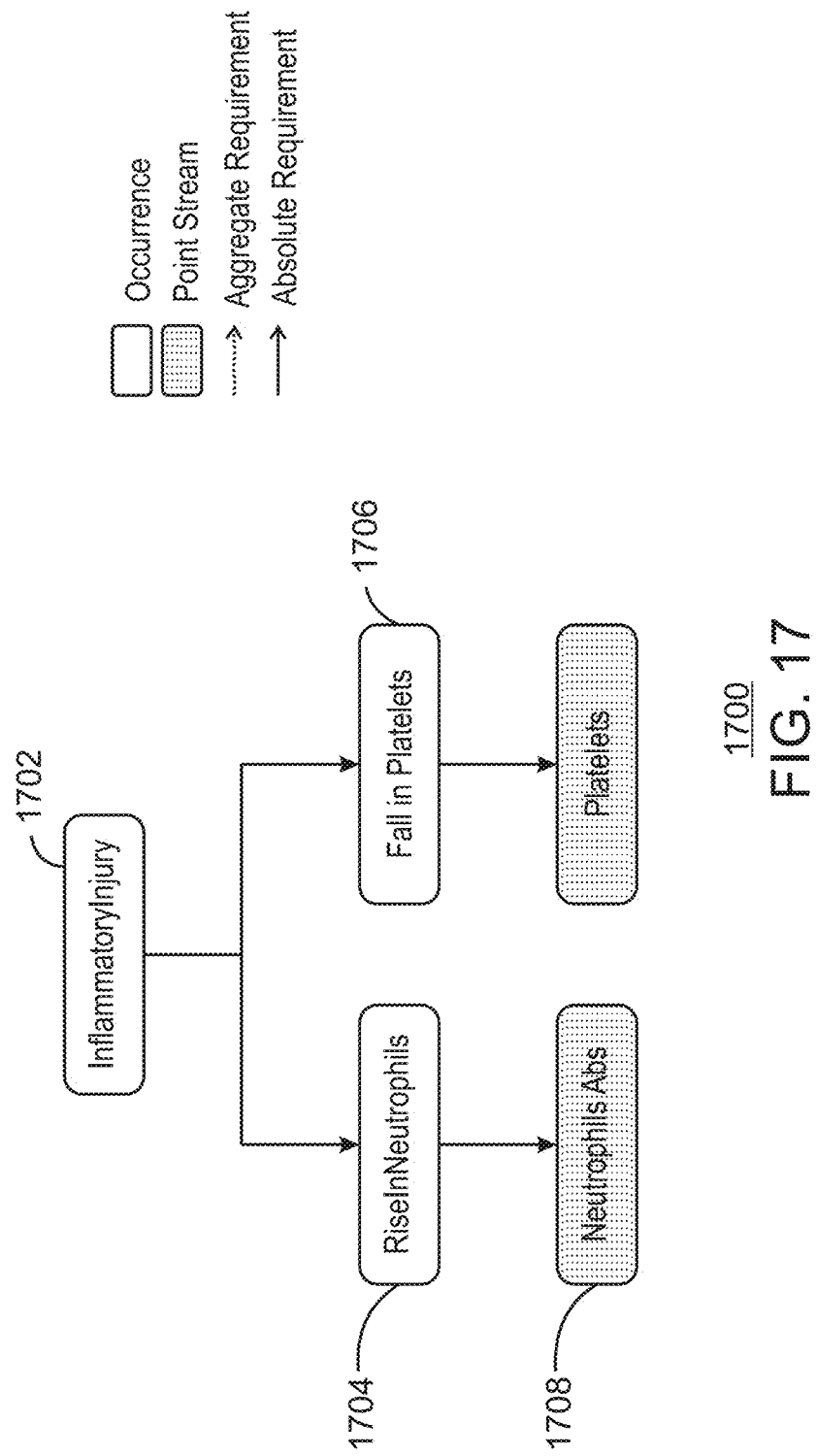
FIG. 17 is tightly associated with FIG. 18 and depicts a PDL Script, Specificity result and dependency diagram for a Binary.

FIGS. 17 and 18 show scenarios for a Binary.

Figure 19:
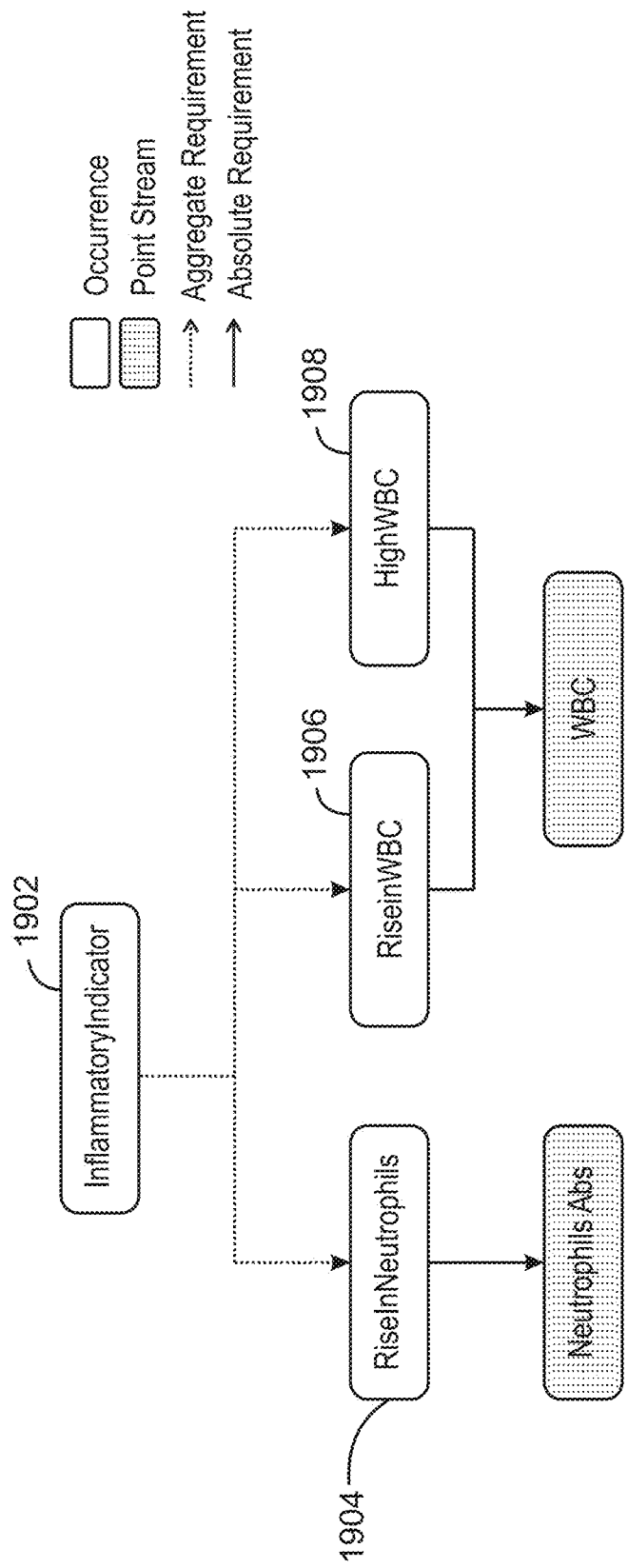
FIG. 19 is tightly associated with FIG. 20 and depicts a PDL Script, Specificity result and dependency diagram for a Classification.

FIG. 19 shows scenarios for a Classification-Based Anchor.

FIG. 20 shows a scenario table 2000 for a classification-based anchor.

Figure 21:
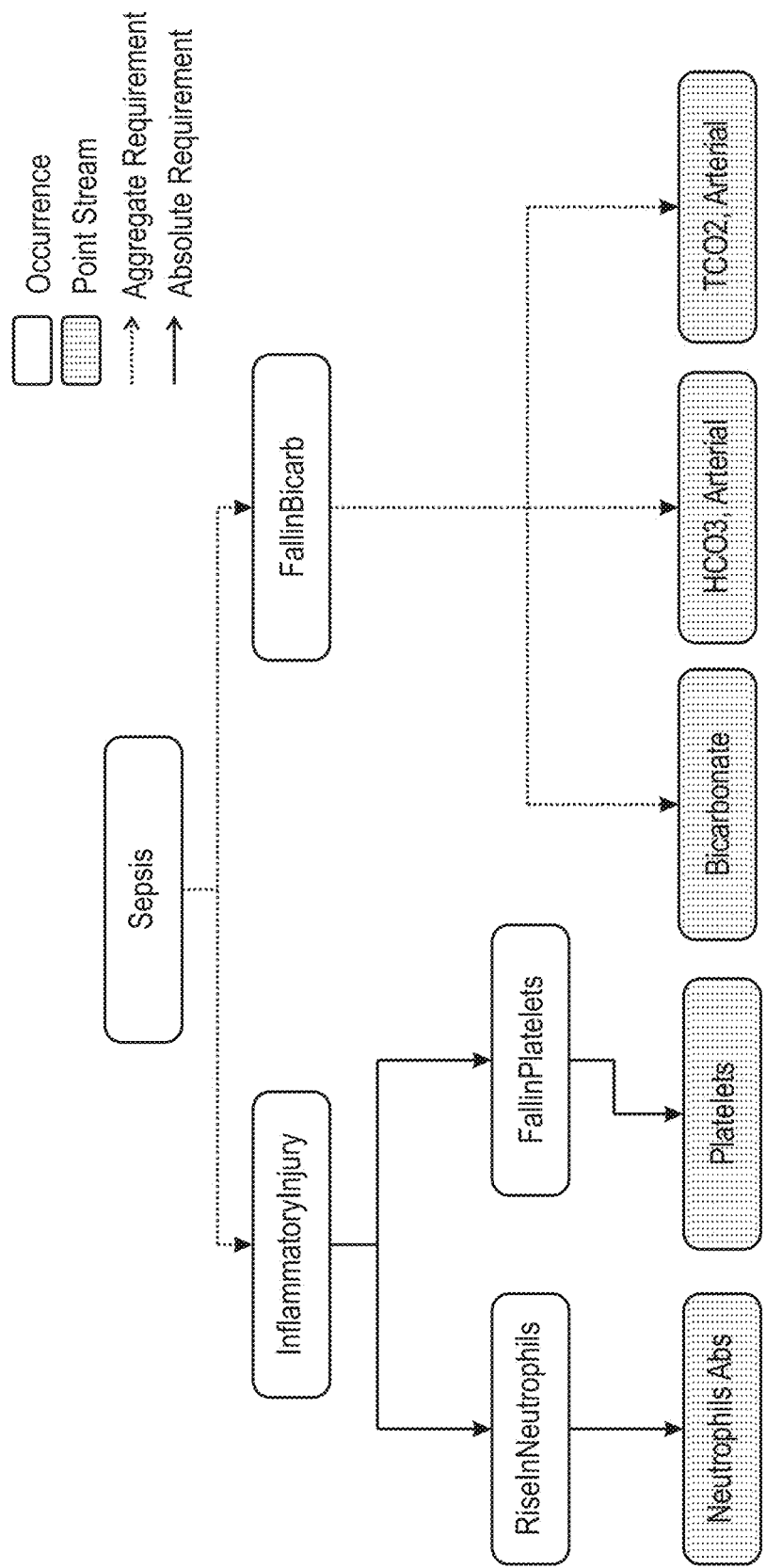
FIG. 21 is associated with FIG. 22 and depicts a PDL Script, Specificity result and dependency diagram for an Image containing a Point Stream Classification.

FIG. 21 shows the results for a representative set of scenarios 2102 for Classification-Based Anchor combined with Point Stream Classifications. FIG. 21 corresponds to a Specificity Marked Pattern, a script that includes "Identify RiseInNeutrophils as Rise in [Neutrophils Abs] where {Candidate.PercentChange>20 and Candidate.Magnitude>4}; Identify FallInPlatelets as Fall in Platelets where {Candidate.PercentChange>30}; Identify InflammatoryInjury as RiseInNeutrophils, FallinPlateletss as within 2d; Classify AnyBicarb as Bicaronate, [HCO3, Arterial], [TCO2, Arterial]; Identify FallInBicarb as Fall in AnyBicarb where {Candidate.PercentChange>20}; Classify Sepsis as InflammatoryInjury, FallInBicarb," and a specificity of 82.35% to Sepsis.

FIG. 22 shows a scenario table 2200 that comprises scenarios for a Classification-Based Anchor combined with Point Stream Classifications.

FIG. 15 shows an example of evaluation for an example Software element within the Simultaneous Multi-Conditional Analysis for an Event. The figure shows the Software element/Specificity Pair 1502 and the Dependency Tree of the Software element. FIG. 16 provides an associated description of scenarios and how they would affect the result (from the Software element in FIG. 15). As described above there are 3 possible results for each evaluation. FIG. 16 shows the results for a representative set of scenarios. The scenario table 1600 shows the condition 1602 of the Point Streams and the results of the pattern identification. For patterns 1604, the columns can include a 1 or a 0. A 1 value indicates that 1 or more instances of the pattern 1604 have been found. A 0 value indicates that no instances of the pattern 1604 were found. For Point Streams, two possible conditions 1606 can apply: 'A' indicates that the Point Stream is available and 'U' indicates that the Point Stream is not available.

Potential may be driven by the hierarchical dependencies within a pattern. In the present embodiment, two types of dependencies exist—actual and aggregate. In some examples, if an event is constructed against the White Blood Count (WBC) Point Stream, then WBC may be an actual dependency for the constructed event. The event cannot be identified without the presence of the WBC Point Stream. In another example, as shown in FIG. 17, a binary 1702 contains two actual inputs 1704 and 1706. If either of the two inputs or elements of the binary 1702 are unavailable, the binary 1702 may be unavailable because a binary 1702 may expect that 2 occurrences be paired together in time. In some embodiments, inputs 1704 and 1706 may flow up the hierarchy. For example, as shown in FIG. 17, Inflammatory Injury 1702 may be actually dependent on RiseInNeutrophils 1704. In turn, RiseInNeutrophils 1704 may be actually dependent on the Neutrophil Abs Point Stream 1708. Given these two relationships, it can be determined that Inflammatory Injury 1702 may be actually dependent on Neutrophil Abs 1708. Given this characteristic of dependency it can be understood that in FIG. 17 Inflammatory Injury 1702 may be actually dependent on RiseInNeutrophils 1704 and FallInPlatelets 1706. FIG. 17 corresponds to a Specificity Marked Pattern, a script that includes "Identify RiseInNeutrophils as Rise in [Neutrophils Abs] where {Candidate.PercentChange>20 and Candidate.Magnitude>4}; Identify FallInPlatelets as Fall in Platelets where {Candidate.PercentChange>30}; Identify.InflammatoryInjury as RiseInNetrophils Preceding FallInPlatelets within 2d," and a specificity of 100.00% to Sepsis.

FIG. 18 illustrates an example for a binary. The scenario table 1800 shows various conditions 1802 of the Point Streams and the results 1804 of the pattern identification.

In some embodiments, an Aggregate Dependency, can indicate that at least one of a set of elements is available. For example, in FIG. 19, Inflammatory Indicator 1902 indicates that one of the 3 sub-elements be available (RiseInNeutrophils 1904 or RiseInWBC 1906 or HighWBC 1908). FIG. 19 corresponds to a Specificity Marked Pattern, a script that includes "Identify RiseInNeutrophils as Rise in [Neutrophils Abs] where {Candidate.PercentChange>20 and Candidate.Magnitude>4}; Identify RiseInWBC as Rise in WBC where {Candidate.PercentChange>20 and Candidate.Magnitude>4}; Identify HighWBC as {Value >14} in WBC; Classify InflammatoryIndicator as RiseInWBC, RiseInNeutrophils, HighWBC," and a specificity of 58.82% to Sepsis.

If the Anchor pattern is not found then the RSM may then navigate the actual and aggregate dependencies to see if the current pattern can contribute to the Maximum Potential value. The RSM may then present the question, "If an additional Point Stream or set of Point Streams were available could the Anchor pattern be identified." The following scenario explanations illustrate details of determining if the anchor pattern can be identified.

In one embodiment, the definition of an Unavailable Point Stream may be one for which there are no points within the time being considered for the given patient. In an alternative embodiment, sparse streams can be determined as Unavailable. For example, if a Bicarbonate Point Stream contains 3 points for 10 days, the Bicarbonate may be considered unavailable. In some embodiments, the determination of unavailable can be based on an allowed variance from hospital protocol. Alternatively, the determination of unavailable can be specified at a point stream level by the researcher such that the patterns defined have a known expectation for the density of data for a given point stream.

In one embodiment individual Occurrence Types can be marked as to be excluded from the calculation of potential. Further, the determination of which Occurrence Types are included in the calculation of potential can be made according to site protocol. For example, if a hospital does not monitor particular biomarkers then the RSM can be configured to exclude patterns dependent on those biomarkers from the system or can mark the biomarker to be excluded from the Potential calculation. In one embodiment there is a differentiation between Global and site potential in which Global Potential may be calculated as if the Point Streams were included.

Potential provides a measure of confidence. In particular, Potential indicates whether a Specificity Value could be potentially low because of the unavailability of data. Another form of confidence can be provided from the Specificity Stack. In one embodiment, the Simultaneous Multi-Condition Analysis does not stop when the Maximum Specificity is determined by continues down the Specificity Stack. This continuation can be complete (For example evaluating the Occurrence Types in the stack) or can be for a given percentage distance from the Maximum Specificity found (e.g. 5%). The count of positive Occurrence Types within a given percentage distance can then be determined (e.g. "6 other patterns have shown positive between 60 and 65% Specificity). In the present embodiment this value may be called the Near Pattern Count. In this way the physician or medical worker can quickly see whether the Specificity presented is based on an isolated pattern or if multiple patterns within the range of Specificity have been shown to be positive. Further, as described below, the entire Specificity stack can be visualized to show the level of confirmation of the Specificity. In one embodiment the phases of a condition are targeted for identification along with and in conjunction with the identification of a condition as a whole. For example, Sepsis may be split up into 6 phases—Inflammation, Early Sepsis, Moderate Sepsis, Severe Sepsis, Profound Sepsis and Late Stage Sepsis. Each phase of sepsis can have unique and/or highly specific patterns that can be used for identification.

In one embodiment, a large set of patients identified by an expert to be Sepsis is further examined by experts to identify the onset time of sepsis and the spans that represent the stages of sepsis. Once these spans are identified they can be isolated as separate regions tagged by stage. The process of pattern identification and enhancement can now proceed in a similar way it was executed for global patient conditions and correlativity metrics can be calculated and persisted.

Once these patterns have been identified along with correlativity metrics, then the momentum of correlativity toward a stage of the condition can be measured over time. If correlativity values indicate a progression (e.g. Inflammation followed by Early Sepsis) confidence metrics can reflect the additional evidence. In one embodiment this pattern is described as a pattern within the Correlativity Metric streams. For example a pattern may be described as:

Identify SepsisStage1 as {value>80} in InflammationCorrelativity;

Identify SepsisStage2 as {value>80} in EarlySepsisCorrelativity;

Identify EarlySepsisLikely as SepsisStage2 following SepsisStage1 within 28 h;

The granularity of the stages may depend on the pattern differentiation between the stages. In this way, patterns that exhibit different (and sometimes conflicting) patterns at different stages can be separated for identification while still being linked to the global pattern of perturbation.

In one embodiment, the stages identified are separated by time segments and a stream subset. In this way, multiple dynamic processes associated with a condition but not tightly correlated to a particular time offset relative to the onset of the condition or the onset of other stages can be isolated and targeted.

One Embodiment of a Method and Process for Generating Rsm Visualization

The creation of Real-time Specificity Time Series along with associated confidence support values (e.g. Potential) provides information that is distilled into a succinct subset of information that can be effectively presented to physicians and other medical care workers.

Figure 23:
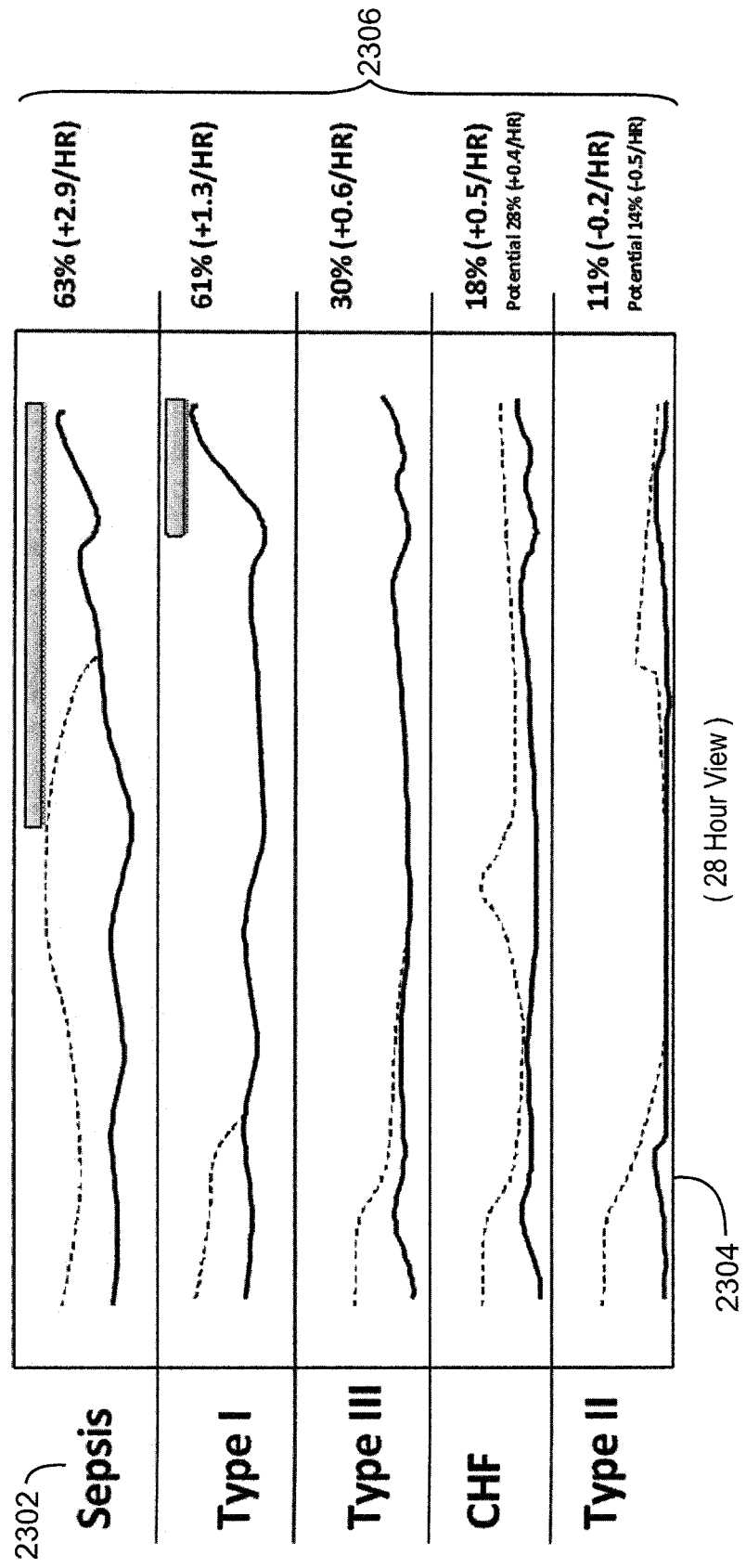
FIG. 23 is a depiction of one embodiment of the Graphical User Interface (GUI) of a Real Time Specificity monitor showing multiple time series of Specificity and Potential for a single patient along with a real time (or near real time) snapshot of current values and visually identified trends.

In the present embodiment the related time series, such as specificity and potential, can be shown together in a monitor that can be placed at strategic locations within the healthcare facility. Alternatively the presentation can be available in various environments including a Web browser, a tablet or slate, as a smart phone application among others. FIG. 23 shows one embodiment of this presentation. In this embodiment, a single patient may be depicted with data presented from the last 28 hours. Specificity streams are ranked by the highest Specificity of the last point of acquired Specificity. As shown in FIG. 23, Sepsis 2302 may be ranked to the top of the monitor. Alternate views can be selected including ranking by other parameters including Maximum Specificity Slope, Maximum Potential or Maximum Potential Slope among others. In the embodiment shown in FIG. 23, the Condition names 2302 are shown on the left side of the monitor followed by a graphical representation of Specificity and Potential within the last 28 hours 2304 followed by the current (i.e. last acquired) values for Specificity, Potential and the rate of change of Specificity and Potential within a certain timeframe 2306 (e.g. 6 hours). The Real-Time Specificity Monitor visualization has the advantage of displaying data in a format that is familiar to healthcare workers. Values, thresholds and trends can be quickly understood. For example, as shown in FIG. 23, the presented patient is clearly being shown to be trending toward Sepsis which indicates to the healthcare worker that comparison to retrospective data indicates that patterns are being found that have been correlated to Sepsis and that within the last 12 hours more and more patterns with greater correlation to Sepsis have been found.

Further, the presentation shown in FIG. 23 indicates Potential which provides a level of confidence regarding the Specificity data. It may be typical that early in a patient stay Potential will be high as data is being collected and new physiological signals are being acquired. Potential then should drop as the hospital protocol is being met. A Potential Gap (as shown in the CHF channel on FIG. 23) indicates a failure of the RSM to acquire the data to analyze the patterns. In an alternate embodiment, the unavailable streams would also be enumerated. Alternatively the unavailable streams could be acquired through interactions with the monitor.

FIG. 23 represents one of several visualizations. In one embodiment, the monitor uses color to indicate severity of the Specificity as well as other visual cues. As shown in FIG. 23 an indicator (iconic or geometric) can highlight aspects of the time series such as a rapid trend. Further, threshold violations, trends and other patterns of Specificity, Potential and Potential Gap can be displayed and/or highlighted.

In one embodiment additional time series are added to the display for example cost and/or quality metrics among others. Further, analysis between these time series and time series of specificity, potential, potential gap, confidence metrics, etc. can be executed, displayed and otherwise utilized.

In some embodiments, interaction with the monitor can provide additional information and clarification. Gestures with a mouse or within a touch environment can be employed to navigate, drill down, zoom and scroll among others. In the present embodiment, the Specificity and Potential time series along with supporting values cannot be altered. The user may annotate visually or with audiovisual notes but the underlying data cannot be altered.

Figure 29:
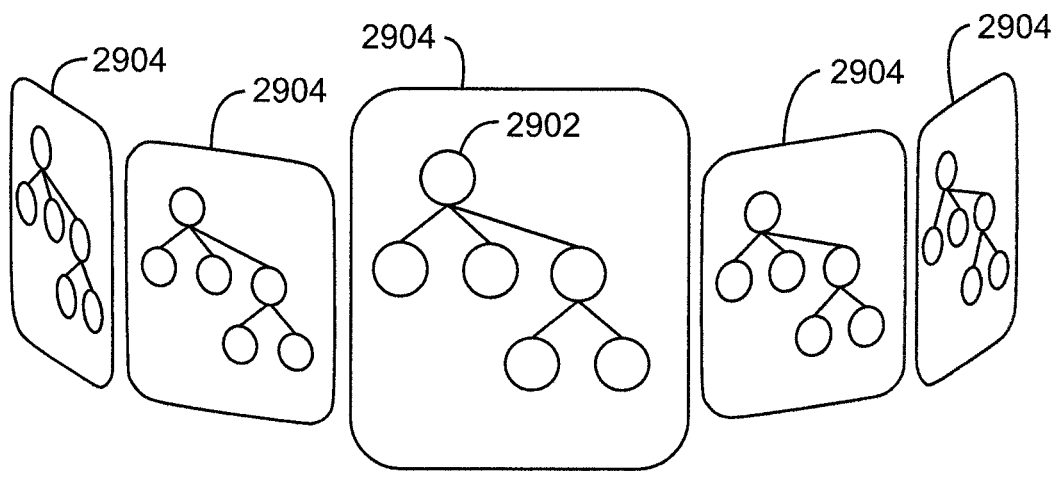
FIG. 29 is a Pattern Catalog navigation GUI for rapidly cycling through patterns, especially patterns currently (or recently) present in a single patient ranked starting with maximum specificity and ranked by specificity.

In one embodiment the interface provides access to views of the underlying patterns as read-only snapshot views of the patient data set with physiological time series related to the pattern fully displayed. As shown in FIG. 29, patterns 2902 may be presented as a carousel of snapshots 2904 of the patterns present (and/or partially present) in the patient within a timeframe and/or globally. Patterns 2902 may be sorted by specificity, potential, potential gap among others. Alternatively the raw signals identified and time-limited by the associated patterns may be presented. In one embodiment, the PDL scripts used to generate the identified patterns 2902 are presented, sorted and available for navigation and review. In one embodiment, the hierarchical and/or relational structure of the patterns 2902 is presented in a tree and/or graph.

Figure 28:
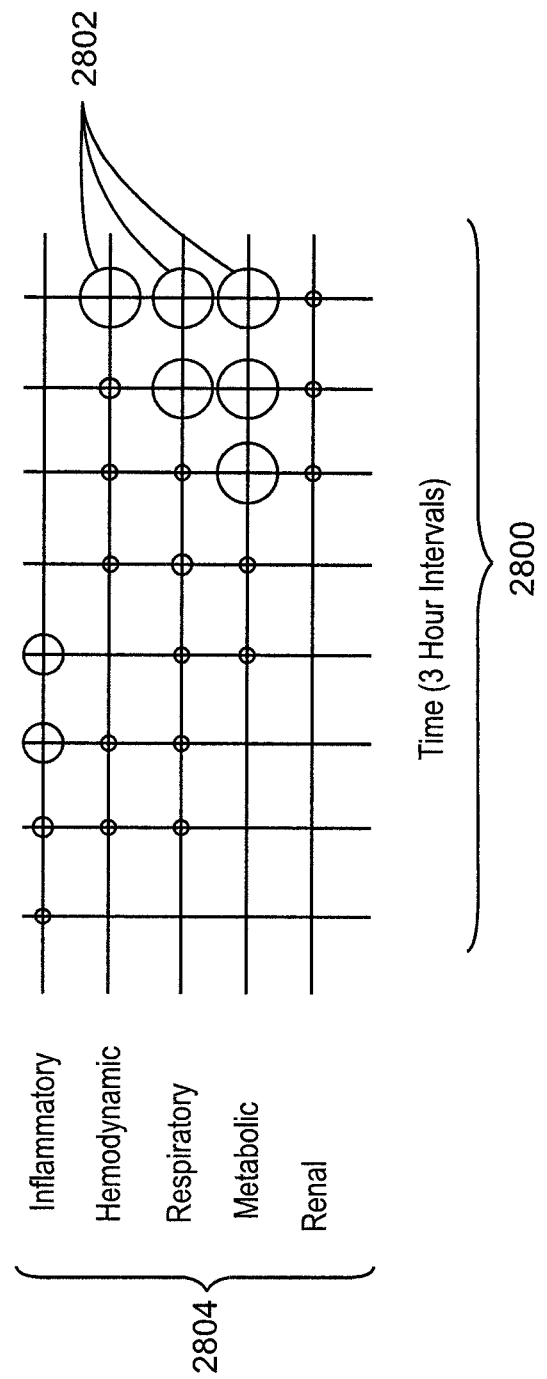
FIG. 28 shows a Graphical User Interface (GUI) display of a Perturbation Evolution Diagram providing a high-level visualization of a Sepsis process evolving in severity over 24 hours within the physiological systems.

In one embodiment, shown in FIG. 28, the evolution of patterns 2902 are presented as a set of circles 2802 (or other shapes) across a field representing a fixed set of physiological systems 2804 on the left and time across the bottom. The circles may be colored by metrics such as severity and/or specificity among others. The diameter of the circles can also be determined by severity and/or specificity among others.

In an alternative embodiment a field representing a fixed set of physiological systems 2804 as large rows or ranks across a plane 2800 is constructed as a background. On top of this background individual pixels (or small shapes) are placed to indicate the identification of an instance of a pattern 2902. This plane 2800 then shows the evolution of perturbation conditions in a patient in the same way that a weather map shows the evolution of a storm. A storm, as referred to herein, includes any indication of an existing or potential physiological perturbation. For example, the background of physiological systems 2804 (such as the inflammatory system, hemostatic system, respiratory system, among others) can provide regional background space in a similar way a map (e.g. a map of the United States or of the State of California, among others) would provide background space or a geospatial point of reference for a weather map. The emergence of small points or growing aggregations of points of color on a particular space or region on the weather map may indicate a combination of precipitation patterns that represent severe weather. In some example, the color intensity or change in color (for example from green to red) can indicate the severity of the weather. In one embodiment, the visualization of a set of physiological systems 2804 can indicate the existence and severity of physiological perturbation. Further, in a weather map, a smattering of dislocated color may indicate small weather patterns that are isolated geographically whereas for the one embodiment of the disclosed physiological map a smattering of color may indicate perturbations occurring in different systems or may indicate isolated biomarker deviation or other disparate phenomenon. With a weather map these isolated smatterings of color may begin to converge into a concentrated or more organized weather pattern over time demonstrating a process that matches historical patterns of evolution. With one embodiment of the physiological map, patterns of perturbation can be shown to be evolving, converging, dissipating or strengthening in a way that mimics the process of severe weather. The weather map metaphor provides a framework to which the healthcare worker can quickly ascertain the conditional snapshot in real time, or after any suitable delay, as well as rapidly absorb the historical evolution of the real time conditions.

In one embodiment each pixel in the plane 2800 is a separate pattern 2902. In an alternative embodiment, a pattern 2902 (or set of patterns) is represented by a single row of pixels on the plane 2800 and the x-axis of the plane 2800 represents time. In this way, the evolution of a condition over time can be visualized in a single image. Alternatively, the pixels on the plane 2800 represent a pattern 2902 or set of patterns and animation is used to demonstrate the evolution of a condition over time. Each pixel in this visualization can further be differentiated by color. Additionally, iconic or textual elements may be overlaid to further communicate features of the condition or the evolution of the condition. The color displayed for each pixel can be chosen by the count of instances of the patterns 2902 represented, severity, correlativity metrics of the pattern 2902, or features of the pattern 2902 among others. In an alternative embodiment, the field represents the one portion of the visualization and a pattern catalog represents another area in the a way that the selection of pixels can drive the display of individual patterns 2902 (in textual, parametric or diagrammatic form) or the selections of patterns 2902 and/or individual elements of the patterns 2902 can indicate which pixel or pixel row is associated.

In one embodiment the background space is defined by the physiologic systems 2804 and then regional space (within the region of each system) is pre-designated as responsive to the detection of a particular occurrence (such as patterns 2902 or images). In this way a particular set of occurrences in a set of systems may reliably produce a set of map patterns 2902 on the map. The map patterns themselves (such as the map pattern of sepsis) can then be imaged and processed by graphical pattern analysis to enhance diagnostic assessment.

In another embodiment the map space or regions is defined as the floor of the hospital, by healthcare worker patient sets, or another grouping. The images and/or the images of expense occurring or associated with those regions may be mapped onto to those regions to provide an overview of timed progression conditions and clinical failures within those regions.

To support visualizations and other methods of segmentation categorization by physiological system may be utilized. Signals, patterns and other elements can be categorized by an expert, through an automated process or a combination of these methods.

In one embodiment each system provides a separate area of the map. These may be default areas or selected by the user. In one embodiment, the areas of the map are standardized so that users become familiar with the standard map and so that patterns are comparable across hospital systems. In one embodiment, the inflammation system is placed on the top row, the clotting system second row, the hematologic system third row, cardiac system fourth, respiratory system fifth, the acid buffer system sixth, renal system seventh, hepatic system eighth, and then additional systems. In some examples, an exogenous action bar may be located above the map, which indicates the occurrence of actions such as central catheter insertion and/or a surgery. Below the map may be therapy actions such as medications and/or fluid infusions. In the sepsis example, the processor may be programmed such that pixels begin to light up green indicating that minor variations, patterns or images have been identified, the number of pixels which light up green may indicate the number of such minor variations, patterns or images. In one embodiment these light up in a particular space within a system region (and/or group of systems regions) designated for a particular occurrence. As the number increases the green area enlarges. As the variations, patterns or images worsen the color can change to yellow and then orange and/or red or another color. As sepsis progresses the area of green increases within a system and spreads or "pops up" separately in other systems with the green pixels turning yellow, and orange and red as the storm (the sepsis) worsens.

To provide enhanced computational transparency the processor may be programmed so that user may elect to see an object flow view or diagram which may be animated to provide timed illustration of the flow of detected occurrences which generated the "weather" map pattern. This may be triggered by mouse over the map pattern or by other methods.

To support visualizations and other methods of segmentation categorization by physiological system may be utilized. Signals, patterns and other elements can be categorized by an expert, through an automated process or a combination of these methods.

In one embodiment the interface, such as shown in FIG. 23, provides for navigation to user interface that provides full interactivity within the patient data set defaulting to the physiological time series related to the maximum specificity pattern but allowing navigation to additional patterns and/or the inclusion of raw physiological time series. In one embodiment, the physician notes (textual, audio, visual, etc.) are accessible along with the physician's notes relationship in time. In an alternative embodiment this User Interface includes the ability to write additional PDL Scripts to investigate the data further.

FIG. 24 depicts an alternative visualization. This visualization may be more suited to a snapshot report which can be delivered to a healthcare worker as a file, or a report, among others. In this visualization, data may be summarized to focus on top ranking conditions 2402 and deltas 2404 (i.e. conditions showing a high rate of change either positive or negative).

In the present embodiment, additional visualizations are provided both for a single patient and for aggregations of patients (e.g. any suitable number of inpatients in the hospital). Data elements include Snapshot Specificity at a point in time, Specificity Range over a time span, Specificity Change over a time span, Specificity Slope over a time span, Specificity Thresholds Met, Directional Events of Specificity among others. Further each of those elements can be presented according to a rank within a patient and/or across patient populations. For example, a healthcare worker can approach the RSM and request a list of the patients sorted by the patient's specificity to CHF. Additionally, the data elements described can similarly be applied to the confidence metrics including Potential, Potential Gap and the Near Pattern Count described above.

Figure 25:
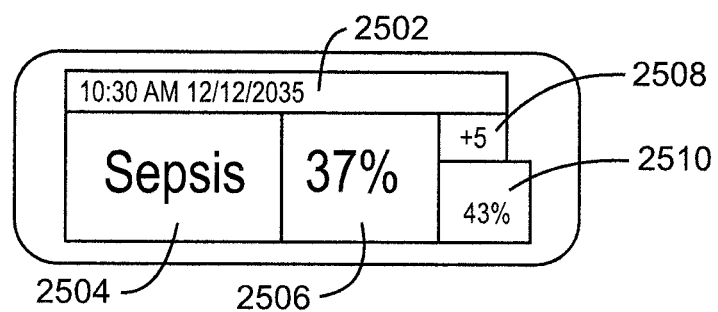
FIG. 25 is a depiction of one embodiment of the human interface of a hardware device into which the described processor is embedded showing Specificity and Confidence Metrics for a single condition.
Figure 26:
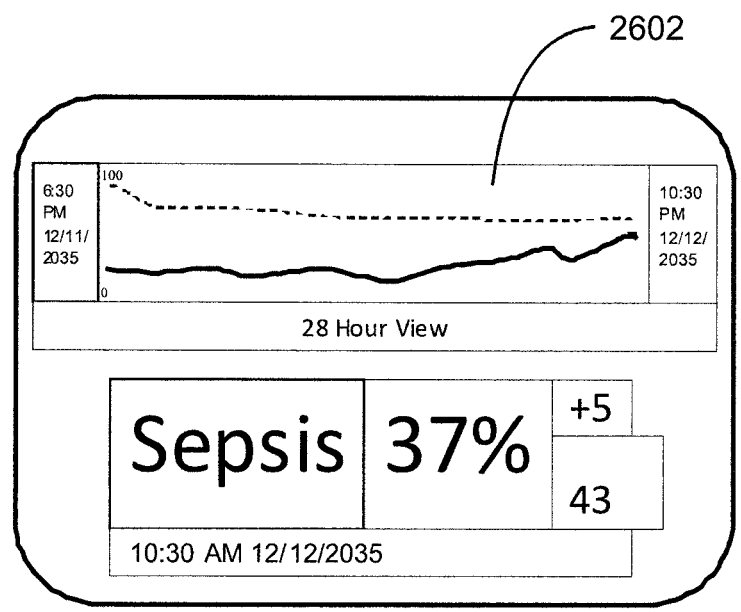
FIG. 26 is a depiction of one embodiment of the human interface of a hardware device into which the described processor is embedded showing Specificity and Confidence Metrics for a single condition as well as 28 hour view of the time series of Specificity and Potential.

In one embodiment a single condition may be monitored (e.g. Sepsis) and the algorithm may be integrated into an embedded hardware environment. FIG. 25 shows an example display of the interface of this embodiment. As shown in FIG. 25, the last Specificity Acquisition Time 2502 is shown, along with four additional pieces of information. First is a textual description of the condition being monitored 2504 (shown here as "Sepsis"). Second is the Snapshot Specificity value 2506 (shown here as "37%"). On the right are two Confidence Metrics: the Near Pattern Count 2508 (shown here as "+5") and Potential 2510 (shown here as "43%"). In an alternative embodiment the interface includes any suitable number of conditions. In another alternative embodiment, the interface includes the graphical display 2602 of the Specificity and Potential time series as shown in FIG. 26.

Figure 27:
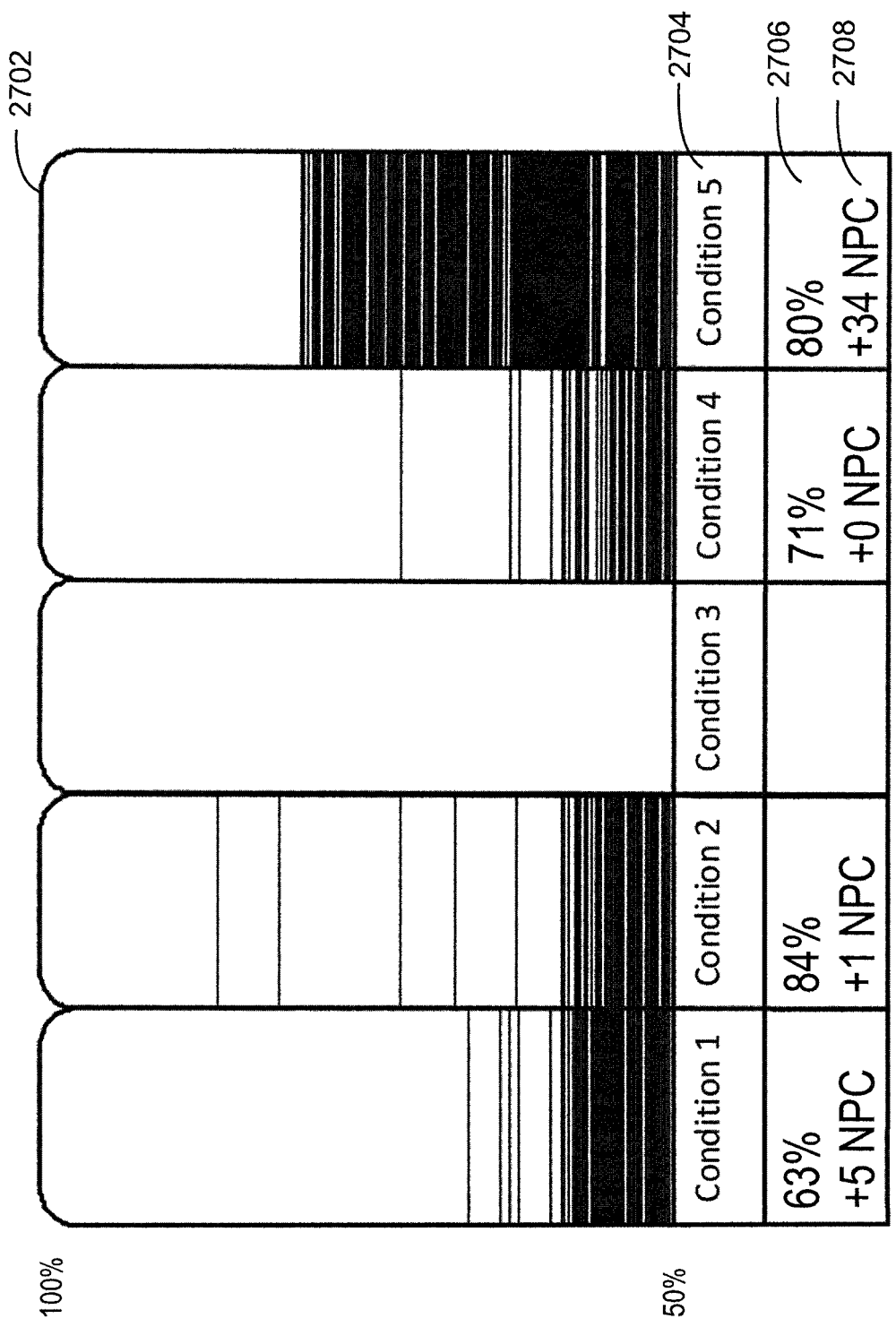
FIG. 27 shows a Graphical User Interface (GUI) display of Specificity Stacks depicting the patterns identified at a single point in time for a single patient.

In one embodiment, the user can choose to review the specificity stack. FIG. 27 depicts a specificity stack display 2702. In this visualization, the specificity stack 2702 is shown for 5 conditions. At the bottom of the stack are 3 pieces of information: the condition label 2704, the maximum specificity 2706 and the near pattern count 2708 (also referred to herein as NPC). For example, as shown in FIG. 27, Condition 1 shows a 63% Maximum Specificity 2706 and a +5 NPC 2708. Above these values is a graphical display of the Specificity Stack 2702 above 50%. In this visualization each pattern shown to be positive is represented by a thin horizon line at the level that represents the corresponding Specificity from the Specificity marked pattern set 302. In this example, Condition 2 has the highest Maximum Specificity (84%), but the confidence metrics are much stronger for Condition 5. For example, some isolated patterns have indicated a high Specificity for Condition 2, but a wide range of patterns have shown Specificity for Condition 5. According to one aspect of the techniques, the presence of any suitable number of isolated patterns that indicated specificity toward a condition is provided by the visualization of the specificity stacks so that the visualization provides additional information to the healthcare worker to mitigate the discounting of such data. In one embodiment the user can interact in various ways with the Specificity Stack visualization 2702 to change the Specificity Range, change the conditions displayed or navigate to the underlying patterns among others.

Further, the Specificity Stack visualization 2702 can be animated to show the dynamism of the physiologic system over time. In this way, the Specificity will appear to move up and down the stacks providing a pictorial evolution that is parallel to the time series of Specificity.

In an alternative embodiment Potential may be also shown or optionally shown on the Specificity Stacks 2702. In an alternative embodiment color, texture, or other differentiating methods may be used. In one embodiment, lines with a level of transparency allowing for overlapping lines to deepen the shade of the color providing a visual sense of density.

The Specificity Stacks can be used to generate additional time-series that can be visualized, analyzed and otherwise utilized. For example, the count of the scripts found positive above a selected specificity and/or potential value (say 65%) tracked over time provides a time series. Multiple time-series based on range can be generated (50-60, 60-70, 70-80, etc.). The Near-Pattern-Count (NPC) 2708 also can be used to generate a time series. Means, medians and averages can be uses as well as relationships between and among specificity, potential, potential gap among others. These time-series can be presented independently or in an overlapping manner.

In one embodiment a relative probability is calculated by a novel modification of the frequentist method of calculating probability. Here the processors search for each value, binary, and/or image (for example of a grouping which has particular relevance to a given condition, such as sepsis) can be considered an "experiment".

The relative probability can then be determined as the sum of the specificities for each experiment divided by the total number of experiments. In one embodiment, experiments with a minimum potential may be included to assure that the probability is not diluted by a large number of experiments with large potential gaps. The calculated probability using this method may be further moved toward the true posterior probability by normalizing the final calculated posterior probability against a population of preprocessed having similar distributions of probabilities which were identified with the conditions under test.

In one embodiment the processor is programmed to adjust global specificity for relational specificity patterns. For example, the processor may be programmed to, upon the detection of a contemporaneous pattern having a high specificity for Thrombotic Thrombocytopenic Pupura (TTP), reduce the specificity reported for the data set for sepsis. Reducing the specificity reported for the data set for sepsis may not indicate that sepsis is not present. In some examples, a portion of the pattern that is suggestive of sepsis can be explained by the presence of TTP. In these examples, the specificity of the data set for sepsis can be reduced when compared to the value which would exist if a pattern providing a high specificity for TTP was absent. Since the overlap of TTP and sepsis may be low in the retrospective data set, the reduction in specificity may not be provided but rather an indication that the probability of sepsis is reduced.

According to one aspect of the present techniques, the calculated potential gap for target conditions like sepsis will rise and fall with the age of data values in the data sets. For example, as the bicarbonate value available to the processor ages it becomes less useful to define specificity and after a prolonged time (such as 48 hours) a normal bicarbonate value will provide little impact on sepsis specificity. In this example, the potential gap rises and falls as a function of the age of the bicarbonate value.

The dynamic patterns of the Potential Gap can be processed by the processor for patterns and these patterns can be used to enhance testing in high risk cases. The time series of the Potential Gap also provides the clinician and user with real time information indicative of the confidence that a given target condition is absent. In one embodiment the potential Gap is divided into components derived from the age of each data component of the potential image and the missing components of the potential image. In an example a patient presents to an emergency room with a skin injury of the knee which demonstrates surrounding inflammation. He has a mild fever and the physician orders a CBC and this returns a white blood cell count 14,400/ml. (mildly elevated) and a platelet count of 160,000 (in the "normal" range). This condition may be cellulitis and easily treated with antibiotics or early necrotizing fasciitis, and/or early generalized sepsis with or without bacteremia, both of which may prompt aggressive intervention. The fever and mildly elevated white blood cell count is a partial image which suggest the possibility of early sepsis but are also present with a mild local infection. Furthermore the physician or nurse practitioner may be rushed and/or may not have experience with subtle signs of necrotizing fasciitis or early sepsis which are often easily discounted and so may discharge the patient with a prescription of antibiotics. According to an embodiment of the present techniques the presence of a skin injury provides a step function in the time series matrix at the time it occurred (entered retrospectively into the medical records). This is an exogenous action affecting the patient. The onset of inflammation at the site becomes another time series beginning when this was first noted and which can be graded over time for severity and increases or decreases based on the grading. The temperature and white blood cell counts are both time series which begin when they were taken and drawn respectively. Any history of immune deficit and treatment which may increase risk of sepsis is a step-function and time series respectively entered into the matrix. These data together along with other patient medical data provide the data set from which the image is derived. This image provides a specificity value which can be a given as a simple low, moderate, or high indication or as a number if sufficient retrospective data sets having similar been processed to generate a valid specificity number for the presence of sepsis. However this image is incomplete because there are missing time series. For example since no differential was ordered, the band count is unavailable so there is a Potential Gap as a function of the lack of band count. For example, if the band count (which was not determined) was high, say 16%, then the specificity result for sepsis would rise from low to high due to this new data. The quantified Potential Gap due to the lack of band count data in the data set (which leaves the image incomplete) is the difference between low specificity and high specificity for sepsis. In one embodiment this is reported to the physician, in another embodiment the band count is automatically ordered by the processor to eliminate the Potential Gap. According to the present techniques other Potential Gap components are also present. For example, if the bicarbonate (which was not determined) was low, say 20, then the specificity result for sepsis would rise from low to high due to this new data. The quantified Potential Gap due to the lack of bicarbonate data in the data set (which leaves the image incomplete) is the difference between low specificity and high specificity for sepsis. The cumulative Potential Gap derived from both the lack of band count data and the lack of bicarbonate data is the difference (the gap) from low specificity of sepsis to nearly 100% specificity for sepsis.

In one embodiment a change in one or more patterns or pattern components component or a change in the specificity feature may trigger the ordering of additional testing. In an example a change in a feature of the specificity for sepsis and/or a change in one or more respiration related parameters (such as, for example, respiration rate, etCO2, tidal amplitude, among others) or of a pattern which includes a respiration related parameter (which may raise the specificity of the data set for sepsis) may be used to trigger a measurement, and/or an increased frequency of measurement, of bicarbonate, pH, or another pH sensitive parameter to enhance the potential specificity of the data set for sepsis (reduce the Potential Gap).

Since the Potential Gap rises and falls with the age of the data, in one embodiment the Potential Gap may be used to enhance the frequency of testing. In one example, after major surgery, the bicarbonate is generally measured daily along with daily electrolyte testing. Yet during advanced sepsis the serum bicarbonate level may decline at a rate of 1 meq per hour. The point at which precipitous collapse is highly variable but many patients will experience respiratory failure when bicarbonate values fall below 12. Therefore the time from the onset of the fall in bicarbonate to the point of respiratory arrest (which is often fatal) may be 16 hours or less which is less than the typical frequency of bicarbonate measurement with routine daily lab. However bicarbonate may decline at a lesser rate. Therefore, the Potential Gap generated by the processor specificity of data sets for sepsis will rise and fall dramatically with the age of the bicarbonate testing given that it is routinely obtained infrequently in comparison to the potential progression rate of sepsis. One solution is to add an indication of bicarbonate to conventional glucometer testing which determines glucose from a tiny drop of capillary blood and is often applied every 8 hours. One method according to the present techniques is to measure and measurement or indication of capillary bicarbonate and/or base deficit. In one embodiment one such indication can be provided as the pH such as a gas equilibrated pH using a handheld glucometer device. The pH may be derived after equilibration with air or may be derived with equilibration with a set value of CO2. In this way this gas equilibrated pH may be more indicative of the bicarbonate (rather than a function of the PCO2 of the capillary blood which is highly variable). One embodiment of the hand-held dual glucometer and gas equilibrated pH testing device comprises a glucometer having a glucose test strip. As is known in the art, the test strip includes a lancet adjacent the end of the strip. The system further comprises a micro-pH probe positioned adjacent the lancet. The Micro pH probe may be comprised of a solid state sensor and a glass or a flouropolymer capillary tube or of other suitable material. In the alternative or in combination the micro pH probe may be a plastic or paper strip having a substrate responsive to optical variation in relation to pH. The system further comprises a photo transmitter and a photo detector capable of producing an output indicative of pH responsive to the variation in color of the substrate induced by the blood pH after gas equilibration. In the alternative or in combination the micro pH probe may be a plastic or paper strip having a substrate responsive to electrical impedance variation in relation to pH. The system further comprises a low voltage source and a sensor capable of producing an output indicative of pH responsive to the variation in impedance of the substrate induced by the blood pH after gas equilibration. A conduit for receiving at least a portion of the blood from the lancet is provided. The conduit may comprise a CO2 permeable membrane which may form at least a portion of the conduit. In one embodiment two adjacent conduits may be provided or a partition may be provided for separating the portion of the blood drop tested for glucose from the portion tested for bicarbonate or pH. In one embodiment the strip has a CO2 permeable membrane covering at least a portion of the strip which allows equilibration with air or a gas source having a fixed partial pressure of CO2. The combined pH and glucose test strip, with the integrated lancet, may be disposable. A partition may be provided to separate blood components of the sample for pH and glucose measurement.

In a similar way other parameters, such as one or more ions, WBC, one or more sepsis biomarkers or other test which demonstrate high or rapidly rising potential with routine monitoring, may also be integrated into a handheld bedside testing device to for testing along with glucose to reduce the variability of the potential.

Using this device, the gas equilibrated pH or another indication of bicarbonate may be routinely determined whenever the glucose is measured and/or a measurement of indicative of bicarbonate may be triggered by the processor when a data feature of a respiration related parameter is identified. Other measurements which reduce the Potential Gap for sepsis may be substituted for the bicarbonate, base deficit, and/or gas equilibrated capillary pH value or triggered in combination with the gas equilibrated capillary pH measurements.

In one embodiment, the processor is programmed to determine at least one specificity or potential for at least one condition, and to determine at least one delay in relation to the at least one specificity or potential. The processor may be further programmed to calculate a quantity metric response to both the specificity and the delay.

FIGS. 30-33 illustrate examples of charts that display patient data. FIG. 30 is an illustration of a chart 3000 that includes patients 3002 ranked according to each patient's specificity 3004 for sepsis. In some embodiments, the chart 300 can also include a change in specificity over time 3006, a potential 3008, and a change in potential 3010.

FIG. 31 is an illustration of a chart 3100 that includes patients 3102 ranked by specificity 3104 for a particular physician 3106. FIG. 32 is an illustration of a chart 3200 that includes patients 3202 ranked by potential 3204 for a particular physician 3206. FIG. 33 is an illustration of a chart 3300 that includes patients 3302 sorted by a change in potential 3304 and by the department 3306 in which the patient 3302 is located.

Figure 34:
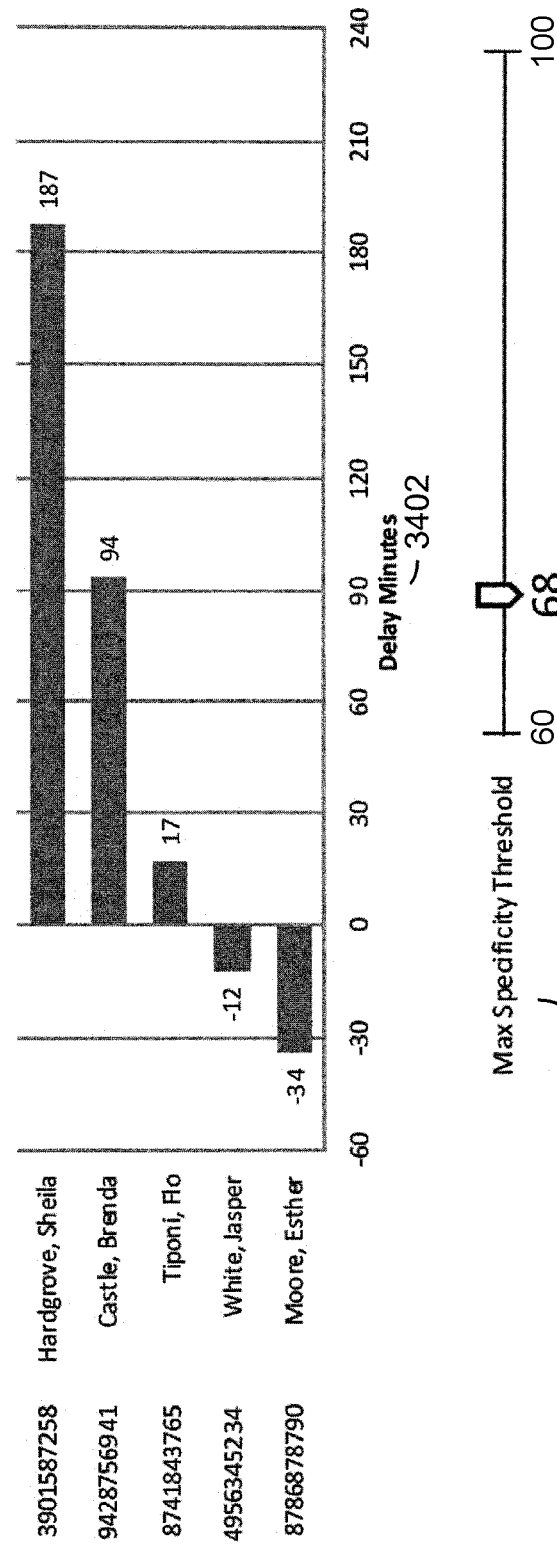
FIG. 34 shows a GUI providing the access to quality measures per physician; in this case the delay minutes against a maximum specificity threshold.

FIG. 34 shows an example of one quality metric or quantity index according to an embodiment of the present techniques which compares diagnostic action and treatment to measures of specificity for sepsis. In the example, the orders of a healthcare worker, the timing of action to those orders (such as the administration of an antibiotic) are compared to the time series of the specificity toward sepsis. In one embodiment the delay time after a target "action specificity" is determined. The target specificity may be the average, a weighted average (or other parametric value of specificity) specificity upon which action is taken which may, for example be calculated by the processor for a large population of patients. Alternatively, the target action specificity a value or weighted range of values range of may be selected by experts or defined in another way. This can be calculated as a diagnostic delay 3402 wherein the delay is defined by a delay in orders for additional and relevant diagnostic testing, and/or a delay in obtaining the diagnostic test such as, for example a blood culture, after the occurrence of the target specificity or by another time relationship to at least one specificity value. In the alternative, or in combination, this can be calculated as a therapeutic delay, wherein the delay is defined by a delay in orders for treatment, for example an antibiotic and/or a delay in delivery of the antibiotic after the occurrence of the target specificity or by another time relationship to at least one specificity value.

In an example, a specificity of 80 may be defined, determined or otherwise selected as the target action specificity 3404. In one example of quality indexing according to on embodiment of the present techniques, this specificity, and each determined specificity after this value, may be multiplied by the delay time after each specificity after the specificity of 80 has been reached (for convenience of use, the product may be divided by 100). In one example, this quality index may be defined as "specificity minutes" such that a diagnostic delay in ordering at least one blood culture after the detection of the quality target specificity may be given in specificity minutes. In an example, a delay by a healthcare worker of 60 minutes, after the processor has detected (and may have provided an output indicating) that the target specificity for sepsis of 80 was identified by the processor, may produce "diagnostic delay index" of 48 specificity minutes. In cases wherein the processor and/or a definitive test eventually defines the specificity as reaching or nearly reaching 100% then delay in testing and treatment is quantified reported as the "specificity indexed treatment delay" or the "specificity indexed diagnostic delay". The time may be compared to the specificity related to time delay as in the example above, and or the potential specificity related to time delay, or potential gap related to time delay. Physicians which act before the target specificity is reached may for example have a negative value for specificity minutes which can indicate a high quantity. The magnitude of the delay index may be compared to the magnitude of the expense to determine the effect of the delay on the expense. For example, a time series of delay minutes may be analyzed against the time series of expense to identify patterns of expense. This can be used to identify and quantify the relationship between expense a specificity, potential, potential gap, and/or confidence metrics among others.

In one embodiment the process can be automated such that physician intervention is not expected and physician related delay is mitigated.

In one embodiment, analysis and identification can be made of gaps between treatment and the time series of specificity. For example, if specificity and/or potential for a condition has not met a particular threshold for a particular condition but treatment, therapy and/or testing associated with the condition exist then quality assurance flags can be turned on to indicate review. The time series of expense may also be considered in this analysis.

One feature and important advantage on an embodiment of the present techniques is that, while assumptions may be applied based on expert analysis to adjust the specificity determinations, the techniques may not employ assumptions defining the priors. In this way, movement of calculated time series of dynamic specificity toward the true time series of dynamic posterior probability is objectively derived with computational transparency as greater number of matrices and patterns become available for comparison over time. As a world repository of matrices and pattern is derived the dynamic time-series of the true posterior probabilities may be approached for many conditions. This iterative method of objectively enhancing posterior probabilities allows visualization and reanimation of the dynamic complex patterns which have the maximum impact on posterior probability. According to one aspect of the present techniques these can be employed for posterior construction of theories defining the conditions, and then to render enhanced diagnostics and treatment which engage the theories, and then these diagnostic and treatment technologies can be tested using the disclosed techniques.

Figure 35:
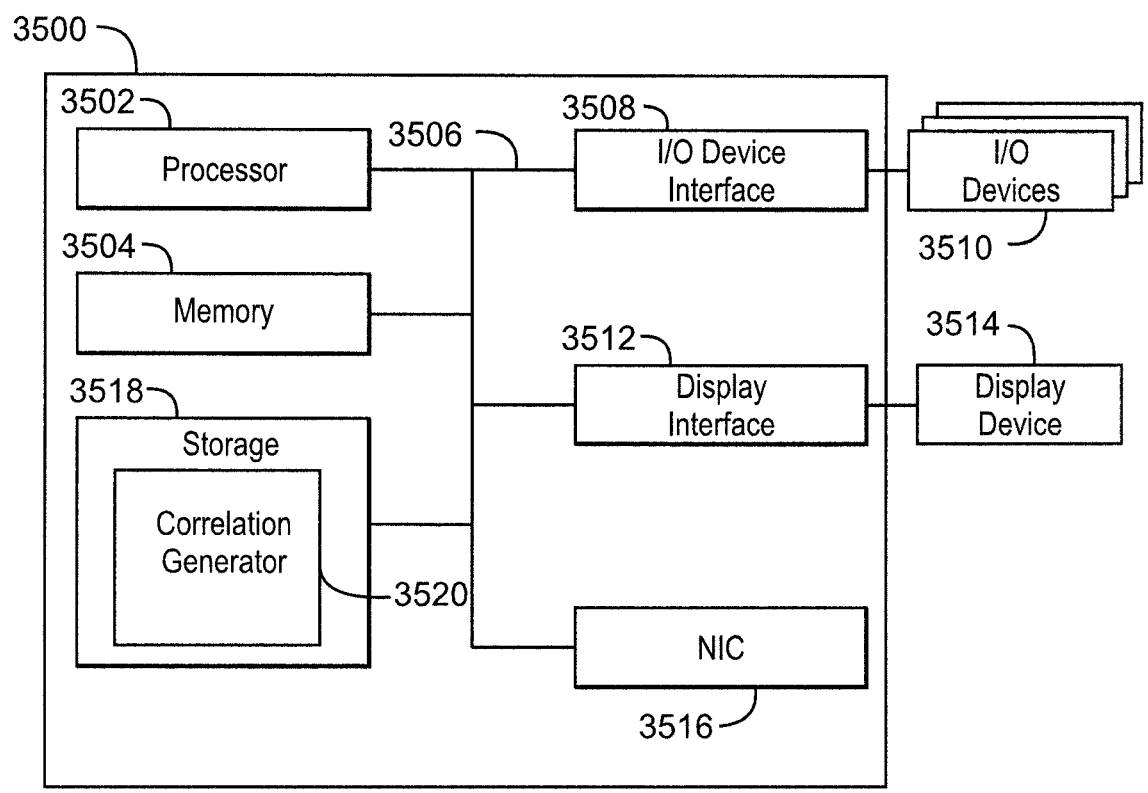
FIG. 35 is a block diagram of an example of a computing system that can provide information about a medical condition

FIG. 35 is a block diagram of an example of a computing system that can provide information about a medical condition. The computing system 3500 may be, for example, a mobile phone, laptop computer, desktop computer, or tablet computer, among others. The computing system 3500 may include a processor 3502 that is adapted to execute stored instructions, as well as a memory device 3504 that stores instructions that are executable by the processor 3502. The processor 3502 can be a single core processor, a multi-core processor, a computing cluster, or any number of other configurations. The memory device 3504 can include random access memory (e.g., SRAM, DRAM, zero capacitor RAM, SONOS, eDRAM, EDO RAM, DDR RAM, RRAM, PRAM, etc.), read only memory (e.g., Mask ROM, PROM, EPROM, EEPROM, etc.), flash memory, or any other suitable memory systems. The instructions that are executed by the processor 3502 may be used to implement a method that includes providing information about a medical condition.

The processor 3502 may be connected through a system interconnect 3506 (e.g., PCI, ISA, PCI-Express, Hyper-Transport®, NuBus, etc.) to an input/output (I/O) device interface 3508 adapted to connect the computing system 3500 to one or more I/O devices 3510. The I/O devices 3510 may include, for example, a keyboard and a pointing device, wherein the pointing device may include a touchpad or a touchscreen, among others. The I/O devices 3510 may be built-in components of the computing system 3500, or may be devices that are externally connected to the computing system 3500.

The processor 3502 may also be linked through the system interconnect 3506 to a display interface 3512 adapted to connect the computing system 3500 to a display device 3514. The display device 3514 may include a display screen that is a built-in component of the computing system 3500. The display device 3514 may also include a computer monitor, television, or projector, among others, that is externally connected to the computing system 3500. In addition, a network interface card (NIC) 3516 may be adapted to connect the computing system 1400 through the system interconnect 3506 to a network (not depicted). The network (not depicted) may be a wide area network (WAN), local area network (LAN), or the Internet, among others.

The storage device 3518 can include a hard drive, an optical drive, a USB flash drive, an array of drives, or any combinations thereof. The storage device 3518 may include a correlation generator 3520 that can generate a correlation related to a medical condition as discussed above. In some examples, the correlation generator 3520 can gather information about the physiological systems of a patient and identify a distress condition based on correlations between data for the physiological system. In some embodiments, the correlation generator 3520 may also provide a visual display of correlations between the physiological systems as a storm spreading across visual depictions of the physiological systems in response to the identification of the distress condition. In some examples, the physiological systems comprise at least two of an inflammatory system, a hemodynamic system, a respiratory system, a metabolic system, and a renal system. In some embodiments, the correlation generator 3520 generates a display that comprises a plurality of regions, wherein each of the plurality of regions displays information for a physiological system. In some examples, the storm spreads across the plurality of regions as each of the plurality of regions displays indications of the distress condition in a physiological system. In some embodiments, the storm develops independently in at least two of the plurality of regions and the storm merges into one storm as the distress condition affects a growing number of the physiological system. In some examples, the storm undergoes a transformation as time elapses. For example, the storm may include different physiological systems as time elapses.

It is to be understood that the block diagram of FIG. 35 is not intended to indicate that the computing system 3500 is to include all of the components shown in FIG. 35. Rather, the computing system 3500 can include fewer or additional components not illustrated in FIG. 35 (e.g., additional memory components, additional modules, additional network interfaces, etc.). Furthermore, any of the functionalities of the code generator 3520 may be partially, or entirely, implemented in hardware and/or in the processor 3502. For example, the functionality may be implemented with an application specific integrated circuit, or in logic implemented in the processor 3502, among others.

Figure 36:
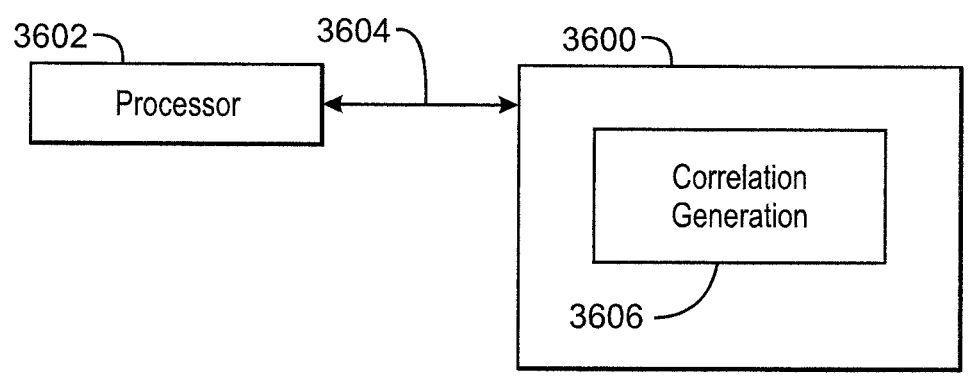
FIG. 36 is a tangible, non-transitory computer-readable media that can provide information about a medical condition.

FIG. 36 is a tangible, non-transitory computer-readable media that can provide information about a medical condition. The tangible, non-transitory, computer-readable medium 3600 may be accessed by a processor 3602 over a computer interconnect 3604. Furthermore, the tangible, non-transitory, computer-readable medium 3600 may include code to direct the processor 3602 to perform the steps of the current method.

The various software components discussed herein may be stored on the tangible, non-transitory, computer-readable medium 3600, as indicated in FIG. 36. For example, a correlation generator 3606 may be adapted to direct the processor 3602 to gather information about the physiological systems of a patient and identify a distress condition based on correlations between data for the physiological system. In some embodiments, the correlation generator 3606 may also provide a visual display of correlations between the physiological systems as a storm spreading across visual depictions of the physiological systems in response to the identification of the distress condition. It is to be understood that any number of additional software components not shown in FIG. 36 may be included within the tangible, non-transitory, computer-readable medium 3600, depending on the specific application.

Conditional language used herein, such as, among others, "can," "may," "might," "could," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated can be made without departing from the spirit of the disclosure. As will be recognized, certain embodiments of the techniques described herein can be embodied within a form that does not provide all of the features and benefits set forth herein, as some features can be used or practiced separately from others. The scope of the techniques is indicated by the appended claims rather than by the foregoing description. All changes which come within the meaning and range of equivalency of the claims are to be embraced within their scope.

What is claimed is:

1. A medical monitoring device for use by a healthcare worker and for monitoring a hospital wide set of patients in real-time or near real-time and for providing computational transparency for the healthcare worker, comprising:

a monitor that:

receives in real-time or near real-time electronic medical records comprising hundreds of sets of contemporaneous time series of physiologic values and time series of laboratory values from the hospital wide set of patients, for each patient of the hospital wide set, applies sequential windows of time so that the time series of physiologic values and the time series of laboratory values of each patient are contained within the sequential windows, and determines a value of a correlation metric for sepsis for each of at least a portion of the sequential windows of time, by:

detecting first patterns of sequential laboratory values and physiologic values of said time series of laboratory values and the time series of physiologic values of each patient, each first pattern being one of a rise pattern of the laboratory values or of the physiologic values over time or a fall pattern of the laboratory values or of the physiologic values over time, detecting relational patterns of sequential laboratory or physiologic values of the time series of each patient, each relational pattern being a combination of one of said rise or fall patterns and at least another said rise or fall patterns occurring in timed relationship to each other, converting the detected first patterns and the detected relational patterns into occurrences, wherein each occurrence includes information for searching for said first pattern or said relational pattern, comparing the detected first patterns and the detected relational patterns to the first patterns and the relational patterns of sequential laboratory values and physiologic values of time series of a representative set of retrospective patient data sets of patients with sepsis, generating, in real-time or near real-time, a time series of the determined values of the correlation metric, and detecting at least one feature of the time series of the values of the correlation metric, the at least one feature being suggestive of sepsis, the at least one feature comprising a value, a trend, slope, derivative or a pattern, and a display processor that:

provides, for each patient of the hospital wide set, at least one visual display comprising a time dimensioned output responsive to the time series of the determined values of the correlation metric in real-time or near real-time, and generates a map of shapes responsive to said occurrences on a background space defined by physiologic systems, and wherein the monitor is further configured to identify in real-time or near real time, each patient of the hospital wide set, with the at least one feature of the time series of the determined values of the correlation metric which is suggestive of sepsis, the monitor further comprising an alarm processor, the alarm processor being responsive to said at least one feature of the time series of the determined values of the correlation metric which is suggestive of sepsis, and to output an alert, and to provide an output of an image highlighting or otherwise distinguishing both the detected first patterns and the relational patterns of sequential laboratory values or physiologic values to which said at least one feature corresponds to provide the healthcare worker with both said alert and computational transparency pertaining to said alert.

2. The device of claim 1 wherein the device determines a plurality of time series of values of a correlation metric for each of a corresponding plurality of distress conditions for each patient of the hospital wide set and provides a display responsive to said plurality of time series of values of said correlation metric so that said healthcare worker can view the display responsive to said plurality of time series of values of the correlation metric for each of the corresponding plurality of distress conditions together for visual comparison.

3. The device of claim 1 wherein the device provides a storm visualization responsive to the time series of values of the correlation metric.

4. The device of claim 1 wherein the device identifies both rise patterns and fall patterns of the time series of the determined values of the correlation metric.

5. The device of claim 4 wherein the device is further configured to identify in real-time or near real-time, each patient of the hospital wide set, with at least one feature of the time series of the determined values of the correlation metric which is suggestive of sepsis, but insufficient for a diagnosis of sepsis and, responsive to that identification, order a biomarker for sepsis or suggest that said healthcare worker order a biomarker for sepsis.

6. The device of claim 1 wherein the device identifies a fall pattern in at least one time series of the determined values of the correlation metric and provides identification of recovery of a distress condition responsive to identifying said fall pattern.

7. The device of claim 1 wherein the display processor further provides a user interface for triggering display of the occurrences responsive to selection of the corresponding shapes on the map.

* * * * *